(12) United States Patent
Rahman et al.

(10) Patent No.: US 8,802,416 B2
(45) Date of Patent: Aug. 12, 2014

(54) THERMOSTABLE ORGANIC SOLVENT TOLERANT PROTEASE FROM GRAM-POSITIVE BACTERIA

(75) Inventors: Raja Noor Zaliha Raja Abd Rahman, Selangor (MY); Abu Bakar Salleh, Selangor (MY); Mahiran Basri, Selangor (MY); Randa Abdelkareem Abusham, Selangor (MY)

(73) Assignee: Universiti Putra Malaysia, Selangor (MY)

( * ) Notice: Subject to any disclaimer, the term of this patent is extended or adjusted under 35 U.S.C. 154(b) by 131 days.

(21) Appl. No.: 12/900,064

(22) Filed: Oct. 7, 2010

(65) Prior Publication Data

US 2011/0097784 A1   Apr. 28, 2011

(30) Foreign Application Priority Data

Oct. 26, 2009   (MY) .................................. 2009-7022

(51) Int. Cl.
*C12N 9/56* (2006.01)

(52) U.S. Cl.
USPC ........................................................ 435/222

(58) Field of Classification Search
CPC ................. C12N 9/54; C12R 1/125
USPC ........................................................ 435/222
See application file for complete search history.

(56) References Cited

PUBLICATIONS

Sambrook et al. [Molecular cloning: a laboratory manual (1989), vol. 3, pp. 8.46-8.63].*
Adinarayana K., et. al., Purification and Partial Characterization of Thermostable Serine Alkaline Protease From a Newly Isolated *Bacillus Subtilis* PE-11., *AAPS Pharmscitech*, 2003, 4(4); p. 56.
Brown, E. D. and Yada, R.Y. 1991. Spin-Labelling and Differential Scanning Colorimetry Study of the Denaturation of Aspartic Proteinases From the Fungi *Endhotia parasitica* and *Mucor. miehei. Agricultural and Biological Chemistry* 55: 1639-1641.
Donaldson, Interactions of Dietary Lead With Fish Oil and Antioxidant in Chicks, *Biological Trace Element Research*, vol. 31, (1991) pp. 215-222.
Escobar and Barnett, Effect of Agitation Speed on the Synthesis of Mucor Miehei Acid Protease, *Enzyme Microb. Technol.*, 1993, vol. 15, December.
Ghorbel B. et al., Stability Studies of Protease From *Bacillus cereus* BG1, *Enzyme Microb. Tech.*, 2003, 32; p. 513-518.
Gouda MK, et. al., Optimization and Purification of Alkaline Proteases Produced by Marine *Bacillus* sp MIG Newly Isolated From Eastern Harbour of Alexandria., *Pol J. Microbiol. Tech.*, 2006, 55; p. 119-126.
Guangrong et. al., Purification and Characterization of a Protease From Thermophilic *Bacillus* Strain HSO8, *African Journal of Biotechnology*, vol. 5(24), pp. 2433-2438, Dec. 18, 2006.

Gupta and Khare, A Protease Stable in Organic Solvents From Solvent Tolerant Strain of *Pseudomonas aeruginosa.*, *Bioresource Technology.*, 2006, 97: 1788-1793.
Jaouadi B., et al., Biochemical and Molecular Characterization of a Detergent-Stable Serine Alkaline Protease From *Bacillus pumilus* CBS With High Catalytic Efficiency, *Biochimie.*, Sep. 2008, 90 (9); p. 1291-1305.
Karadzic I, et. al., Purification and Characterization of a Protease From *Pseudomonas seruginosa* Grown in Cutting Oil., *J. Biosc.ience and Bioengineering*, 2004, 98; p. 145-152.
Kim SS, et al., Purification and Characterization of a Novel Extracellular Protease From *Bacillus cereus* KCTC 3674, *Arch Microbiology*, Jun. 2001, 175 (6) p. 458-461.
Kumar CG, et al., Microbial Alkaline Proteases From a Bioindustrial View Point, *Biotech. Adv.*, 1999, 17; p. 561-594.
Kumar, C. G., Tiwari, M. P. and Jany, K. D. 1999. Novel Alkaline Serine Proteases From Alkalophilic *Bacillus* spp, Purification and Some Properties. *Process Biochemistry* 34: 441-449.
Laemmli UK, Cleavage of Structural Proteins During the Assembly of the Head of Bacteriophage T4., *Nature*, 1970, 227 (5259); p. 680-685.
Li, S., HE, B., Bai, Z. and Ouyang, P. 2009. A Novel Organic Solvent-Stable Alkaline Protease From Organic Solvent-Tolerant *Bacillus licheniformis* YP1A. *Journal of Molecular Catalysis B: Enzymatic* 56: 85-88.
Malathu R. et al., Characterization and Wash Performance Analysis of Microbial Extracellular Enzymes From East Calcutta Wetland in India, *Am J Appl. Science*, 2008, 5; p. 1650-1661.
Moon, et al., Purification and Characterization of an Extracellular Alkaline Protease From *Bacillus Subtilis* RM615, *J. Korean Biochem.*, (1994), vol. 27, No. 4, pp. 323-329.
Ogino, H., Yasui, K., Shiotani, T., Ishihara T. and Ishikawa, H. 1995. Organic Solvent-Tolerant Bacterium Which Secretes an Organic Solvent-Stable Proteolytic Enzyme, *Applied and Environmental Microbiology* 61(12): 4258-4262.
Rahman, Rnza. et al., Purification and Characterisation of Heat-Stable Alkaline Protease From *Bacillus stearothermophilus* F1., *Appl. Microbiol. Biot.*, 1994, 40; p. 822-827.
Rahman, Rnzr et. al., Physical Factors Affecting the Production of Organic Solvent-Tolerant Protease by *Pseudomonas aeruginosa* Strain K., *Biosource Technol.*, 2005, 96; p. 429-436.
Reddy, L. V. A., Wee, Y. J. and Ryu, H. W. 2008. Purification and Characterization of an Organic Solvent and Detergent-Tolerant Novel Protease Produced by *Bacillus* sp RKY3. *Journal of Chemical Technology & Biotechnology* 83(11): 1526-1533.
Salvesen, G., and Nagase, H. 1989. Inhibition of Proteolytic Enzymes. In Beynon, R. J., and Bond, J. S. (Eds.), Proteolytic Enzymes: A Practical Approach. (pp. 83-104). Oxford: IRL Press.
Sarath G. et al., Protease Assay Methods, *Proteolytic Enzymes: A Practical Approach*, 1989, p. 25-55.

(Continued)

*Primary Examiner* — Tekchand Saidha
(74) *Attorney, Agent, or Firm* — Edwards Wildman Palmer LLP; Ralph A. Loren; Richard B. Emmons

(57) ABSTRACT

The present invention relates to a thermostable protease useful as an enzyme for industrial use, a gene encoding the same and a method of producing the enzyme by genetic engineering technique. More particularly, the present invention discloses a thermostable organic solvent tolerant protease and its code gene and application. The invention also discloses a method for preparing protease by isolating from *Bacillus subtilis* isolate Rand bacteria. The activity and stability of protease (preferably named Rand protease) at high temperature, and can be used in fields of washing agent industry, foodstuff industry, biological pharmacy and environmental biological technique.

5 Claims, 19 Drawing Sheets

(56) References Cited

PUBLICATIONS

Sareen and Mishra, Purification and Characterization of Organic Solvent Stable Protease From *Bacillus licheniformis* RSP-09-37, *Appl. Microbiol. Biotechnol.*, Jun. 2008, 79 (3); p. 399-405.

Schmidt, F.R. (2004). Recombinant Expression Systems in the Pharmaceutical Industry. Applied Microbiology Biotechnology 4: 363-372.

Slepecky, R. A. (1992). What Is *Bacillus*? in DOI, R. H. and MacGloughlin, M. (Eds), *The Biology of Bacilli: Application to Industry*, (pp. 1-21). USA: Butterworth-Heineman.

Tamura K., et al., MEGA-4: Molecular Evolutionary Genetics Analysis (MEGA) Software Version 4.0, *Mol. Biol. Evol.*, 2007, 245; p. 1596-1599.

Tang, X.Y., Pan, Y., Li, S. and HE, B.F. 2008. Screening and Isolation of an Organic Solvent-Tolerant Bacterium for High-Yield Production of Organic Solvent-Stable Protease. *Bioresource Technology* 99(15): 7388-7392.

Thompson, JD et. al., Clustal W. Improving the Sensitivity of Progressive Multiple Sequense Alignment Through Sequence Weighting, Position-Specifc GAP Penalties and Weight Matrix Choice, *Nucleic Acids Res.*, 1994, 22; p. 4673-4680.

Wang SL et. al., Production of a Surfactant-and Solvent-Stable Alkaphilic Portease by Bioconversion of Shrimp Shell Wastes Fermented by *Bacillus subtilis* TKU07, *Process Biochecm.*, 2006, 41; p. 1545-1552.

Wang SL, et al., A Solvent-Stable Metalloprotease Produced by *Bacillus* sp. TKU004 and Its Application in the Deproteinization of Squid Pen for Chitin Preparation, *Enzyme Microb Tech*, 2006, 39; p. 724-731.

Yandri, et. al., The Chemical Modification of Protease Enzyme Isolated From Locale Bacteria Isolate, *Bacillus subtilis* ITBCCB148 With Cyanuric Chloride-Polyethylenglycol, *European Jounral of Scientific Research*, vol. 23, No. 1 (2008) pp. 177-186.

Yossan, S., Reungsang, A. and Yasuda, M. 2006. Purification and Characterization of Alkaline Protease From *Bacillus megaterium* Isolated From Thai Fish Sauce Fermentation Process. *Science Society of Thailand* 32: 377-383.

Zhu, W., Cha, D., Cheng, G., Peng, Q. and Shen, P. 2007. Purification and Characterization of a Thermostable Protease From a Newly Isolated *Geobacillus* sp. YMTC 1049. *Enzyme and Microbial Technology* 40: 1592-1597.

Irfan, M., et al. 2011. Exploitation of Different Agro-Residues for Acid Protease Production by *Rhizopus* sp. In Koji Fermentation, *IJAVMS* vol. 5, Issue 1, 43-52.

Ogino H, Peptide Synthesis Catalyzed by Organic Solvent-Stable Protease From *Pseudomonas aeruginosa* PST-01 in Monophasic Aqueous-Organic Solvent Systems, *J Bioscience and Bioengineering*, 1999, 88 (5), p. 513-518.

Ogino H., Purification and Characterization of Organic Solvent-Stable Protease From Organic Solvent-Tolerant *Psuedomonas aeruginosa* PST-01, *J Biosc Ience and Bioengineering*, 1999; 87(1), p. 61-68.

Li Z. et al., Production of a Novel Bioflocculant by *Bacillus licheniformis* X14 and Its Application to Low Temperature Drinking Treatment, *Bioresource Technology*, Jul. 2009, 100 (14) p. 3650-3656.

Rao MB, et al., Molecular and Biotechnological Aspects of Microbial Proteases, *Microbiology Mol Biol Review*, Sep. 1998, 62 (3), p. 597-635.

Schmidt LM, et al., Detection of Pasteuria Penetrans Infection in Meloidogyne Arenaria Race 1 in Planta by Polymerase Chain Reaction, *FEMS Microbiol. Ecol.*, Jun. 1, 2004, 48 (3), p. 457-464.

Gupta R. et al., An Overview on Fermentation, Downstream Processing and Properties of Microbial Alkaline Proteases, *Appl. Microbiol. Biotechnol.*, Dec. 2002, 60 (4); p. 381-395.

Reddy LV, et al., Optimization of Alkaline Protease Production by Batch Culture of *Bacillus* sp. RKY3 Through Plackett-Burman and Response Surface Methodological Approaches, *Bioresource Technol.*, May 2008, 99 (7); p. 2242-2249.

Brown Ed, et al., A Kinetic and Equilibrium Study of the Denaturation of Aspartic Proteinases From the Fungi, *Endothia parasitica* and *Micor miehei.*, *Biochim. Biophys. Acta.*, Feb. 15, 1991, 1076 (3); p. 406-415.

Vazquez JC, Constipation, Haemorrhoids, and Heartburn in Pregnancy, *Clin Evid (Online)*, Feb. 20, 2008; PII 1411.

Gupta and Khare, Enhanced Production and Characterization of a Solvent Stable Protease From Solvent Tolerant *Pseudomonas aeruginosa* PSEA., *Enzyme Micros. Tech.*, 2007, 42, p. 11-16.

Ghorbel B. et al., Stability Studies of Protease From *Bacillus cereus* BGI, *Enzyme Micros. Tech.*, 2003, 32; p. 513-518.

Rahman, Rnzr et. al., Physical Factors Affecting the Production of Organize Solvent-Tolerant Protease by *Pseudomonas aeruginosa* Strain K., *Biosource Technol.*, 2005, 96; p. 429-436.

Ogina H. et al., Organic Solvent-Tolerant Bacterium Which Secretes an Organic Solvent-Stable Proteolytic Enzyme, *Appl Environ Microbiol.*, 1995, 61; p. 4258-4262.

Gupta A. et al., Purification and Characterization of a Solvent Stable Protease From *Pseudomonas seruginosa* PSEA, *J Chromatogr A*, 2005, 1069; p. 155-161.

Wang SL, et al., A Solvent-Stable Metalloprotease Produced by *Bacillus* sp. TKU004 and Its Application in the Deproteinization of Squid Pen for β-Chitin Preparation, *Enzyme Micros Tech*, 2006, 39; p. 724-731.

Gouda MK, et. al., Optimization and Purification of Alkaline Proteases Produced by Marine *Bacillus* sp. MIG Newly Isolated From Eastern Harbour of Alexandria., *Pol J. Microbiol. Tech.*, 2006, 55; p. 119-126.

*Bacillus subtilis* Strain Rand 16S Ribosomal RNA Gene, Partial Sequence Accession No. EU233271.

\* cited by examiner

CGCTGGCGGCGTGCCTAATACATGCAAGTCGAGCGGACAGATGGGAGCTTGCTCCCTGAT 60

GTTAGCGGCGGACGGGTGAGTAACACGTGGGTAACCTGCCTGTAAGACTGGGATAACTCC 120

GGGAAACCGGGGCTAATACCGGATGCTTGTTTGAACCGCATGGTTCAAACATAAAAGGTG 180

GCTTCGGCTACCACTTACAGATGGACCCGCGGCGCATTAGCTAGTTGGTGAGGTAATGGC 240

TCACCAAGGCAACGATGCGTAGCCGACCTGAGAGGGTGATCGGCCACACTGGGACTGAGA 300

CACGGCCCAGACTCCTACGGGAGGCAGCAGTAGGGAATCTTCCGCAATGGACGAAAGTCT 360

GACGGAGCAACGCCGCGTGAGTGATGAAGGTTTTCGGATCGTAAAGCTCTGTTGTTAGGG 420

AAGAACAAGTACCGTTCGAATAGGGCGGTACCTTGACGGTACCTAACCAGAAAGCCACGG 480

CTAACTACGTGCCAGCAGCCGCGGTAATACGTAGGTGGCAAGCGTTGTCCGGAATTATTG 540

GGCGTAAAGGGCTCGCAGGCGGTTCCTTAAGTCTGATGTGAAAGCCCCCGGCTCAACCGG 600

GGAGGGTCATTGGAAACTGGGGAACTTGAGTGCAGAAGAGGAGAGTGGAATTCCACGTGT 660

AGCGGTGAAATGCGTAGAGATGTGGAGGAACACCAGTGGCGAAGGCGACTCTCTGGTCTG 720

TAACTGACGCTGAGGAGCGAAAGCGTGGGGAGCGAACAGGATTAGATACCCTGGTAGTCC 780

ACGCCGTAAACGATGAGTGCTAAGTGTTAGGGGGTTTCCGCCCCTTAGTGCTGCAGCTAA 840

CGCATTAAGCACTCCGCCTGGGGAGTACGGTCGCAAGACTGAAACTCAAAGGAATTGACG 900

GGGGCCCGCACAAGCGGTGGAGCATGTGGTTTAATTCGAAGCAACGCGAAGAACCTTACC 960

AGGTCTTGACATCCTCTGACAATCCTAGAGATAGGACGTCCCCTTCGGGGGCAGAGTGAC 1020

AGGTGGTGCATGGTTGTCGTCAGCTCGTGTCGTGAGATGTTGGGTTAAGTCCCGCAACGA 1080

GCGCAACCCTTGATCTTAGTTGCCAGCATTCAGTTGGGCACTCTAAGGTGACTGCCGGTG 1140

ACAAACCGGAGGAAGGTGGGGATGACGTCAAATCATCATGCCCCTTATGACCTGGGCTAC 1200

ACACGTGCTACAATGGACAGAACAAAGGGCAGCGAAACCGCGAGGTTAAGCCAATCCCAC 1260

AAATCTGTTCTCAGTTCGGATCGCAGTCTGCAACTCGACTGCGTGAAGCTGGAATCGCTA 1320

GTAATCGCGGATCAGCATGCCGCGGTGAATACGTTCCCGGGCCTTGTACACACCGCCCGT 1380

CACACCACGAGAGTTTGTAACACCCGAAGTCGGTGAGGTAACCTTTATGGAGCCAGCCGC 1440

CGAAGGTGGGACAGATGT 1458

Figure 7

Lane M: Molecular mass marker proteins, Lane 1 and 2: Protease of *B. subtilis* strain Rand

SEQUENCE LISTING

```
<160> NUMBER OF SEQ ID NOS: 3

<210> SEQ ID NO 1
<211> LENGTH: 1458
<212> TYPE: DNA
<213> ORGANISM: Bacillus subtilis

<400> SEQUENCE: 1
cgctggcggc gtgcctaata catgcaagtc gagcggacag atgggagctt gctccctgat      60
gttagcggcg gacgggtgag taacacgtgg gtaacctgcc tgtaagactg ggataactcc     120
gggaaaccgg ggctaatacc ggatgcttgt ttgaaccgca tggttcaaac ataaaaggtg     180
gcttcggcta ccacttacag atggacccgc ggcgcattag ctagttggtg aggtaatggc     240
tcaccaaggc aacgatgcgt agccgacctg agagggtgat cggccacact gggactgaga     300
cacggcccag actcctacgg gaggcagcag tagggaatct tccgcaatgg acgaaagtct     360
gacggagcaa cgccgcgtga gtgatgaagg ttttcggatc gtaaagctct gttgttaggg     420
aagaacaagt accgttcgaa tagggcgta cctttgacggt acctaaccag aaagccacgg    480
ctaactacgt gccagcagcc gcggtaatac gtaggtggca agcgttgtcc ggaattattg     540
ggcgtaaagg gctcgcaggc ggttccttaa gtctgatgtg aaagccccccg gctcaaccgg    600 ggagggtcat tggaaactgg ggaacttgag tgcagaagag gagagtggaa ttccacgtgt     660
agcggtgaaa tgcgtagaga tgtggaggaa caccagtggc gaaggcgact ctctggtctg     720
taactgacgc tgaggagcga aagcgtgggg agcgaacagg attagatacc ctggtagtcc     780
```

```
acgccgtaaa cgatgagtgc taagtgttag ggggtttccg cccttagtg ctgcagctaa      840 cgcattaagc actccgcctg gggagtacgg tcgcaagact gaaactcaaa ggaattgacg      900
ggggcccgca caagcggtgg agcatgtggt ttaattcgaa gcaacgcgaa gaaccttacc      960
aggtcttgac atcctctgac aatcctagag ataggacgtc cccttcgggg gcagagtgac     1020
aggtggtgca tggttgtcgt cagctcgtgt cgtgagatgt tgggttaagt cccgcaacga     1080
gcgcaaccct tgatcttagt tgccagcatt cagttgggca ctctaaggtg actgccggtg     1140
acaaaccgga ggaaggtggg gatgacgtca aatcatcatg ccccttatga cctgggctac     1200
acacgtgcta caatgacag aacaaagggc agcgaaaccg cgaggttaag ccaatcccac      1260
aaatctgttc tcagttcgga tcgcagtctg caactcgact gcgtgaagct ggaatcgcta     1320
gtaatcgcgg atcagcatgc cgcggtgaat acgttcccgg gccttgtaca ccgcccgt      1380 cacaccacga gagtttgtaa cacccgaagt cggtgaggta acctttatgg agccagccgc     1440
cgaaggtggg acagatgt                                                  1458

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gagtttgatc ctggctcag                                                   19

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cggctacctt gttacgactt                                                  20
```

THERMOSTABLE ORGANIC SOLVENT TOLERANT PROTEASE FROM GRAM-POSITIVE BACTERIA

RELATED APPLICATIONS

This present patent application claims priority to Malaysian patent application number 2009-7022, filed on Oct. 26, 2009, the entirety of which is herein incorporated by reference.

SEQUENCE LISTING

The instant application contains a Sequence Listing which has been submitted in ASCII format via EFS-Web and is hereby incorporated by reference in its entirety. Said ASCII copy, created on Dec. 7, 2010, is named 87313732.txt and is 2,885 bytes in size.

FIELD OF INVENTION

The present invention relates to a protease derived from gram-positive microorganism. More particularly, the present invention relates to isolation, optimization, purification and characterization of thermostable and organic solvent tolerant protease.

BACKGROUND OF INVENTION

Currently enzymes have attracted the attention of the world due to their wide range of industrial applications in many fields including organic synthesis, clinical analysis, pharmaceuticals, detergents, food production and fermentation. Enzymes are gradually replacing the use of harsh chemicals in various industrial processes (Malathu et al., 2008). Proteases represent one of the three largest groups of industrial enzymes and account for about 60% of the total worldwide sale of enzymes. Enzymes are established active ingredients of detergents and cleaning agents. Proteases induce degradation of protein-based soiling on the items to be cleaned, such as textiles or hard surfaces. Various gram-positive microorganisms are known to secrete extracellular and/or intracellular protease at some stage in their life cycles. Many proteases are produced in large quantities for industrial purposes. A negative aspect of the presence of proteases in gram-positive organisms is their contribution to the overall degradation of secreted heterologous or foreign proteins.

The classification of proteases found in microorganisms is based on their catalytic mechanism which results in four groups: the serine proteases; metalloproteases; cysteine proteases; and aspartic proteases.

Proteases are degradative enzymes which catalyze the hydrolysis of peptides. They are obligatory components for microorganisms which are involved in the utilization of proteinous nutrient, releasing of protein, zymogen activation, autolysis, spore germination and other physiological phenomena (Cappuccino and Sherman, 1992). Proteases represent the class of enzymes which occupy a pivotal position with respect to their physiological roles as well as their commercial applications. They perform both degradative and synthetic functions (Rao et al., 1998). Proteases are one of the most important groups of industrial enzymes and account for nearly 60% of the total enzyme sale (Brown and Yada, 1991; Escobar and Barnett 1993; Adinarayana et al., 2003).

Thermostable enzymes can be obtained from mesophilic and thermophilic organisms; even psycrophiles have some thermostable enzymes. Thermophiles represent an obvious source of thermostable enzymes, being reasonable to assume that such character will confer their proteins a high thermal stability. The industrial use of proteases in detergents or for leather processing requires that the enzyme be stable at higher temperatures. Thermostable proteases are advantageous in some applications because higher processing temperatures can be employed, resulting in faster reaction rates, increase in the solubility of nongaseous reactants and products, and reduced incidence of microbial contamination by mesophilic organisms.

Accordingly, the present invention relates to a thermostable protease useful as an enzyme for industrial use, a gene encoding the same and a method of producing the enzyme by genetic engineering technique.

SUMMARY OF THE INVENTION

Accordingly, the present invention relates to a biologically pure culture of a microorganism producing protease, wherein the microorganism is *Bacillus subtilis* isolate Rand obtained from environmental samples (deposited under the accession number EU233271). The *Bacillus subtilis* isolate Rand includes the following properties 16s RNA amplification size of 1458 bp, Nucleotide sequence of SEQ ID NO 1, and morphology and physiological properties such as aerobic, gram positive, endo-spore forming, rod-shape bacteria, having a width between 0.7 and 0.8 µm and length between 2.5 and 3.0 long, having 2% tolerant to NaCl, positive for citrate and nitrate test, fermenting D-glucose, L-arabinose, D-xylose, D-mannitol and D-fructose, capability of hydrolyzing starch, gelatine, casein, Tween 80 and propionate Moreover, *Bacillus subtilis* isolate Rand provides working temperature range from 30° C. to 60° C. with an optimum temperature at least 50° C., working pH in the range between pH 5 and 6.

Accordingly, the protease being isolated from *Bacillus subtilis* isolate Rand provides growth activity: upon cultivation in a production media composition of nitrogen source such as peptone iv and ions including $Ca^{2+}$, $K^+$ and $Na^+$; stable in organic solvent such as n-tetradecane, n-hexadecane, n-dodecane, p-xylene, n-hexane, benzene, n-decane and butanol at 55° C. for at least 30 min; temperature activity and stability: upon incubation of the protease at temperatures between 37° C. and 80° C. for 30 minutes, the activity of the protease is substantially 100%; after 30 minutes' incubation at 60° C.; pH stability: upon incubation at 37° C. for 24 hours between pH values between 4 and 9.0, the protease production is stable at pH 7; agitation activity: upon incubation at 37° C. for 24 hours between agitation of 0 to 250 rpm, an optimum growth of the protease is at 200 rpm; inoculums size: upon incubation at 37° C. for 24 hours using a working inoculum size between 1% (v/v) and 11% (v/v), an optimum inoculum size for the protease is 5% (v/v); working carbon source of maltose, sucrose, glucose, galactose, trehalose, starch, rhamnose melibiose, myo-inositol, lactose, mannitol, sorbitol, fructose and arabinose; working inorganic nitrogen source such as ammonium sulfate, ammonium nitrate, ammonium chloride, ammonium ferric sulfate, ammonium heptamolybdate, urea, di-ammonium hydrogen phosphate and sodium nitrate; working organic nitrogen source such as casein, casamino acid, yeast extract, tryptone, peptone, beef extract, protease peptone and corn steep liquor; working amino acids such as L-lysine, glutamic acid, glycin, arginine, cysteine, alanine, arabinose and homoserine; working metal ions such as $Na^+$, $K^+$, $Mg^{2+}$ and $Ca^{2+}$ from sodium chloride, potassium dihydrogen phosphate, magnesium sulphate and calcium chloride, sodium chloride, potassium dihydrogen phosphate, magnesium sulphate, calcium chloride, manganese chloride, ferric chloride, cobalt chloride, copper chloride, zinc chloride and barium chloride.

In addition, the present invention also relates to a purified protease which is derived from *Bacillus subtilis* isolate Rand having the following properties: an apparent molecular weight of 28 kD determined by SDS-PAGE; a pH stability with buffers (including sodium acetate, sodium phosphate acetate, sodium phosphate, Tris-Cl, glycine-NaOH and sodium hydrogen carbonate) ranging from pH 5 to pH 11 at 25° C.; a working temperature (optimum value of 60° C.) in the range between 37° C. and 70° C. at pH 7.0; organic solvents [organic solvents includes n-dodecane (log P 6.6), diethyleether (log P 4.3), p-xylene (log P 3.1), toluene (log P 2.5), chloroform (log P 2.0), benzene (log P 2.0), acetone (log P 0.23), butanol (log P 0.8) and ethanol (log P 0.24)] stability of 25% (v/v) of organic solvents for 30 min and at 37° C.; working inhibitors including ethylenediaminetetraacetic acid (EDTA), bestatin, pepstatin A, phenylmethanesulfonyl fluoride (PMSF), 1,4-Dithio-$_{DL}$-threitol (DTT), and 2-Mercaptoethanol for 30 min at ° C.; working metal ions such as $K^+$, $Na^+$, $Mg^{2+}$, $Fe^{2+}$, $Co^{2+}$, $Cu^{2+}$, $Zn^{2+}$ and $Li^{2+}$ and substrate specificity with natural substrate including casein, albumin, haemoglobin and azocasein, the stability of the purified protease is substantially 100%; with azocasein after 30 minutes incubation at 37° C.

It is said that the *Bacillus subtilis* isolate Rand is purified Rand proteas and is thermostable with organic solvent tolerant properties.

Yet, the present invention also describes a method of producing a purified Rand protease wherein the method includes isolating *Bacillus subtilis* isolate Rand producing thermostable organic solvent tolerant protease, identify the *Bacillus subtilis* isolate Rand, obtaining thermostable organic solvent tolerant protease, optimizing the protease production, purifying the protease, obtaining a purified protease, characterizing the purified protease.

Finally, the present invention describes a use of purified Rand protease for the manufacturing of industrial application products.

BRIEF DESCRIPTION OF THE DRAWINGS

The accompanied drawings constitute part of this specification and include an exemplary or preferred embodiment of the invention, which may be embodied in various forms. It should be understood, however, the disclosed preferred embodiments are merely exemplary of the invention. Therefore, the figures disclosed herein are not to be interpreted as limiting, but merely as the basis for the claims and for teaching one skilled in the art of the invention.

In the appended drawings:

FIG. 7 shows 16S rRNA nucleotide sequence of *Bacillus subtilis* isolate Rand (SEQ ID NO 1).

DETAILED DESCRIPTION OF THE INVENTION

Figure 1:
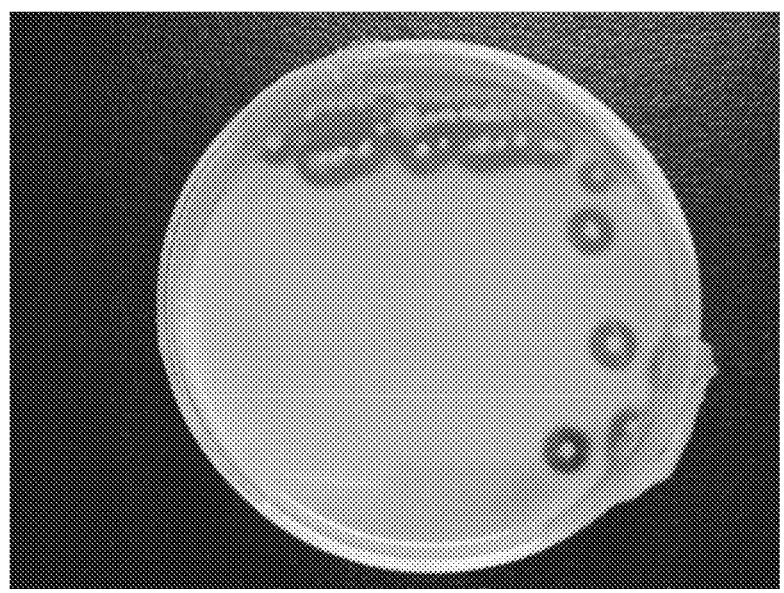
FIG. 1 shows zone formation by bacterium on SMA plate.

While the specification concludes with claims particularly pointing out and distinctly claiming the invention, it is believed the present invention will be better understood from the following description.

All percentages are by weight of total composition unless specifically stated otherwise.

All ratios are weight ratios unless specifically stated otherwise.

All cited references are incorporated herein by reference in their entireties. Citation of any reference is not an admission regarding any determination as to its availability as prior art to the claimed invention.

DEFINITIONS

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand. As used herein "amino acid" refers to peptide or protein sequences or portions thereof. A "polynucleotide homolog" as used herein refers to a gram-positive microorganism polynucleotide that has at least 80%, at least 90% and at least 95% identity to *B. subtilis* isolate Rand, under conditions of high stringency and which encodes nucleotide/nucleic acid sequence having protease activity.

The terms "isolated" or "purified" as used herein refer to a nucleic acid or nucleotide that is removed from at least one component with which it is naturally associated.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. It must be noted that as used herein and in the appended claims, the singular forms "a," "an," and "the" include plural referents unless the context clearly dictates otherwise. The invention discloses a thermostable organic solvent tolerant protease and its code gene and application. The invention also discloses a method for preparing protease by isolating from *Bacillus subtilis* isolate Rand bacteria. The activity and stability of protease (preferably named Rand protease) at high temperature, and can be used in fields of washing agent industry, foodstuff industry, biological pharmacy and environmental biological technique.

INDUSTRIAL APPLICATION

In a method of producing a product, Rand protease holds greater potentials in industrial application which mainly trying to focus on reducing energy as well as time and money. The enzyme will be a good addition to the enzyme sales as it is applied in dairy, detergents, pulp and papers, pharmaceuticals industries and many more. The organic solvent fastness alkaline proteinase is high in specific activity, strong in solvent tolerance, wide in action pH scale, strong in thermostable and strong alkalinity tolerance and the like.

BEST MODE FOR CARRYING OUT THE INVENTION

It is to be understood that while the invention has been described in conjunction with the preferred specific embodiments thereof, the foregoing description is intended to illustrate and not limit the scope of invention.

According to the first stage of the present invention is to screen and isolate thermostable, organic solvent tolerant protease from bacteria from hot spring water from Selayang and Batangkali (60, 54, 51 and 50° C.) and contaminated soils (54° C.) from Port Dickson, Malaysia were carried out. Nine isolates were positive on skim milk agar 10(%). A newly isolated soil bacterium, *Bacillus subtilis* isolate Rand (preferably known as Isolate Rand) was establish, by which the bacterium exhibits an extracellular protease activity, and being identified based on 16S rRNA analysis (GenBank EU233271). Isolate Rand was isolated from contaminated soils from Port Dickson and showed the highest activity (34.9 U/ml). Moreover, crude protease activity was enhanced by n-hexadecane (log P 8.8), n-tetradecane (log P 7.6), n-dodacane (log P 6.0), n-decane (log P 5.6), n-hexane (log P 3.5), p-xylene (log P 3.1), toluen (log P 2.5), benzene (log P 2.0) and butanol (log P 0.80). Indeed, optimum activity of the crude protease is exhibited at 60° C. The protease appear having the capability to be stable and retain its full activity after 30 minutes incubation from 4 to 55° C., while 81% of the activity was still retained at 60° C.

The second stage of the present invention relates to optimization of protease production condition. Indeed, maximum protease production was achieved when grown in 50 ml medium (pH 7.0). Inoculum size of 5% (v/v) proved to be the best for protease production, with an optimum temperature of 37° C., when grown under shaking condition of 200 rpm. Moreover, all carbon sources tested decreased protease production, except lactose and melibiose whereby protease production was improved. Indeed, Tryptone and ammonium heptamolybdate were found to be preferred organic nitrogen and inorganic nitrogen sources. Also, protease production was stimulated by l-lysine and calcium.

In the third stage of the present invention relates to purification of protease obtained from the *Bacillus subtilis* isolate Rand. The purification was perform by means of a combination of two purification steps, hydrophobic interaction chromatography on Octyl-Sepharose and gel filtration. Indeed, Rand protease was purified by 19.3 fold purification and 60.5% recovery. A purified protease migrated as a single band with a molecular mass of ~28 kDa on SDS-PAGE was establish. The purified protease is preferably known as purified Rand protease. The purified protease is capable of hydrolyzing azocasein at optimum temperature of 60° C. However, the enzyme lost its activity with a half life of more than 20 min at 60 and 65° C. An optimum activity of the protease was observed at pH 7.0 and it was stable in the pH range of pH 6.5 to 10. Purified Rand protease exhibited high stability in the presence of n-dodecane (log P 6.6), diethyleether (log P 4.3), p-xylene (log P 3.1), toluene (log P 2.5), benzene (log P 2.0), acetone (log P 0.23), butanol (log P 0.8) and ethanol (log P 0.24). The protease activity was completely inhibited by PMSF while 43 and 30% reduction of protease activity was observed in the presence of EDTA and DTT respectively. Protease activity retained about 95% and 63% in the present of aminopeptidases (Bestatin) and aspartic proteases inhibitor (pepstatin A). Among the metal ions, $Zn^{2+}$ was found to stimulate protease activity by 175%. Protease activity was enhanced by 105%, 112% and 105% respectively $Na^+$, $K^+$ and $Li^+$. For substrate specificity, Rand protease was able to hydrolyze several native proteins such as casein, haemoglobin, albumin and azocasein.

The enzyme catalysis in the organic solvents is becoming increasingly important for the synthesis of many useful compounds and optical resolution of chiral compounds. Purified Rand protease was found to be stable in the presence of hydrophobic and hydrophilic organic solvents and it is believed that Rand protease could be a very useful biocatalyst for peptide synthesis in the presence of organic solvent. These results suggest that this protease may be a novel solvent-stable protease. Indeed, the objective of producing Rand protease by isolate Rand is to be capable of proving a shorter incubation period, which will decrease operational cost.

EXAMPLES

Bacterial Sources

The bacteria were obtained from hot spring water from Selayang and Batangkali (60, 54, 51 and 50° C.) and contaminated soils (54° C.) from Port Dickson, Malaysia.

Isolation and Screening of Proteolytic Bacteria

To isolate pure bacterial colonies from the TSB media, serial dilution were performed. One mL of each culture was transferred into mL sterile normal saline, and 0.1 mL of the diluted sample spread on nutrient agar plates. The plates were incubated at different temperature (70, 60, 55 and 50° C.) for 24 h. Each pure colony was tested for protease activity on 3, 5, and 10 percent (w/v) skim milk agar and incubated at different temperature (70, 60, 55 and 50° C.) for 24 h 48 h and 72 h. Formation of clearing zone surrounding the colonies was considered positive, forming of zone on high concentration of skim milk agar indicating to high protease activity. The positive isolates were then tested for protease production in production media.

Glycerol Stock Culture

Single colony of pure cultures of protease—producing bacteria each was incubated into 10 ml tryptone soy broth. The cultures were incubated at 50° C. overnight, and the bacteria centrifuged at 12,000×g and 4° C. for 10 min. Each bacterial pellet was suspended in a sterilized solution of 15% glycerol in tryptone soy broth (v/v) and mixed well. The bacterial solution was transferred into 1.5 ml Eppendorf tubes and store at −80° C.

Preparation of Inoculum

The inoculum was prepared by inoculating a loopful of bacteria from the stock culture into 10 ml tryptone soy broth in universal bottle and incubated in shaker (150 rpm) at 50° C. overnight The cells were harvested by centrifugation at 12,000×g for 10 min and the bacterial pellets were dissolved in physiological saline 0.85% (w/v) NaCl to give an absorbance reading of ($AB_{600}$=0.5). Inoculum size at $AB_{600}$=0.5, 5% (v/v) of the isolate was used for both effect nutritional factors and physical factors on protease production.

Contaminated and hot environment may provide a suitable environment for the growth of micro-organisms to produce thermostable, organic-solvent tolerant proteases. Several samples were obtained from the hot spring water and contaminated soil from Selayang, Batangkali and Port Dickson, Malaysia. From the comprehensive screening on Skim Milk Agar (SMA), ten isolates (labelled as L1, L2, BK, BK1, BK2, PD, PD1, PD2, PD and Rand) demonstrated a large zone of hydrolysis around the colony on the SMA (FIG. 1). This indicated their good growth and the ability to produce extracellular proteolytic enzymes. For the purpose of conducting a quantitative measurement of the proteolytic activity, all the ten isolates were grown in liquid production media. The extra-cellular enzyme was harvested and assayed according to the modified method proposed by Rahman et al. (1994) using azocasein as a substrate. All of these isolates were found to be able to produce protease (Table 1). Among the ten isolates, Rand was detected to have the highest protease activity (34.9 U/ml).

TABLE 1

Protease production from different isolates

| Isolates | Protease production (U/ml) | | |
|---|---|---|---|
|  | 24 h | 48 h | 72 h |
| Port Dickson's care service: | | | |
| PD | 1.7 | 7.1 | 9.0 |
| PD1 | 0.5 | 1.1 | 2.0 |
| PD2 | 0.4 | 0.0 | 0.0 |
| PD3 | 0.0 | 0.0 | 0.5 |
| Rand | 34.9 | 23.5 | 7.0 |
| Batang Kal's hot spring water: | | | |
| BK | 0.7 | 1.3 | 1.9 |
| BK1 | 0.9 | 1.9 | 2.7 |
| BK2 | 0.07 | 0.5 | 0.7 |
| Selayang's hot spring water: | | | |
| SL1 | 0.0 | 10.0 | 7.1 |
| SL2 | 15.0 | 4.3 | 1.1 |

The Effect of Different Production Media on Protease Production

Effect of media on protease production was studied by cultivation of isolate Rand in 5 different production media. All the production media were adjusted to pH 7.0 and bacterial cultivations were incubated at 150 rpm, 50° C. for 24, 48 and 72 h. The bacterium which showed highest activity of protease was selected to further study in this project. The compositions of each media were listed as below.

M1 casein 3%, $NaNO_3$ 0.5%, $K_2HPO_4$ 0.5%, $MgSO_4.7H_2O$ 0.02%, $NaCO_3$ 1%. (Abdulrahman and Yasser, 2004).

M2 (g/L) $CaCl_2.2H_2O$ 0.5, $K_2HPO_4$ 0.2, $MgSO_4.7H_2O$ 0.5, NaCl 0.1 and 1% peptone, type iv. (Rahman et al., 2003).

M3 (g/L) glucose 10.0 g, peptone 5.0 g, yeast extract 5.0 g, $KH_2PO_4$ 1 g, $MgSO_4.7H_2O$ 0.2 g. (Mabrouk et al., 1999).

M4 (g/L) peptone 10.0 g, $(NH_4)_2SO_4$ 1 g, $KH_2PO_4$ 0.5 g, $MgSO_4.7H_2O$ 0.3 g, $CaCl_2.2H_2O$ 1 g, NaCl 1.0 g, glycerol 10 ml. (Mabrouk et al., 1999).

M5 glucose, 0.5% (w/v); peptone 0.75% (w/v); and salt solution, 5% (v/v) ($MgSO_4.7H_2O$, 0.5% (w/v); $KH_2PO_4$, 0.5% (w/v); and $FeSO_4.7H_2O$, 0.01%. (Adinarayana et al., 2003).

Figure 2:
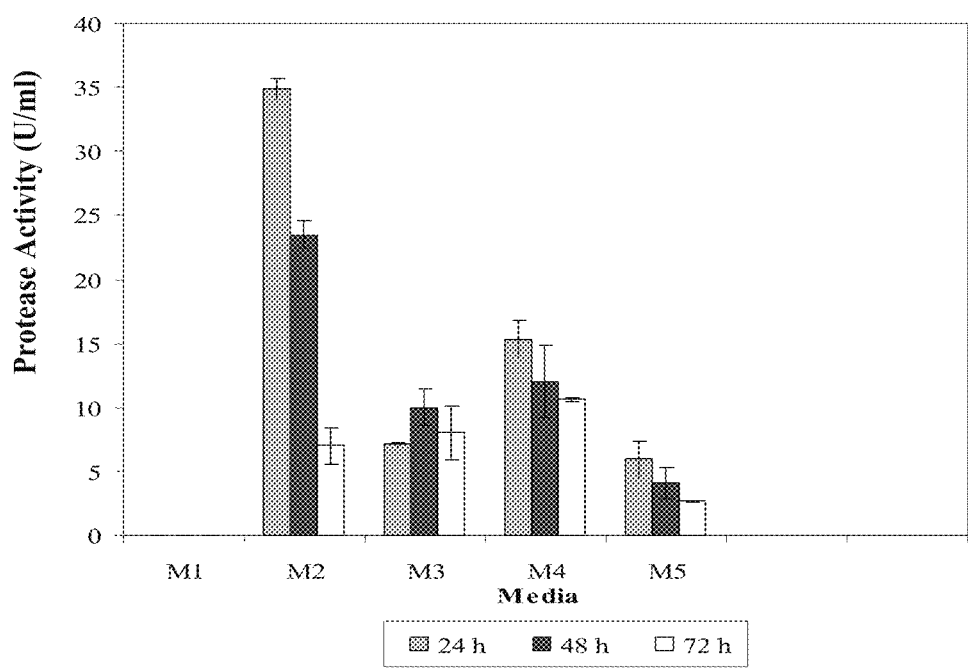
FIG. 2 shows effect of media on protease production. Culture media were incubated at 50° C. with shaking at 150 rpm for 72 h.

All the media were found to support bacterial growth, but the protease activity for each medium was revealed to be different (FIG. 2). Among the media, M1 was found to completely inhibit the protease activity, while the highest protease activity (34.9 U/ml) was observed in M2 after 24 h of incubation (FIG. 2). The Medium M2 was found as the most suitable medium for the maximum protease production of isolate Rand. This might be attributed to the suitability and availability of the medium composition such as organic nitrogen source (peptone, type iv) and ions $Ca^{2+}$, $K^+$ and $Na^+$ in enhancing the production of isolate Rand protease.

Assay of Protease Activity

Protease activity was determined by a slight modification method of Rahman et al. (1994). Freshly prepared azocasein with concentration of 0.5% (w/v) in Tris-Cl (0.1 M), $CaCl_2$ (2 mM) pH 7.0 buffers was used as a substrate. 100 μl of enzyme was added into each vial bottle containing 1 ml of substrate. Blank reagent as a control was done by replacing the enzyme solution with Tris-Cl (50 mM, pH 7.0) buffer. Each sample was run in triplicate. Enzyme-substrate mixture was incubated at 50° C. for 30 min at 150 rpm in water bath shaker. The reaction was terminated by adding 1.1 ml of Trichloroacetic Acid (TCA) 10% (w/v) and allowed to stand at room temperature (25-27° C.) for 30 min. The precipitate protein was separated by centrifuging at 13000×g for 10 min. 1 ml of supernatant fluid was transferred into test tube contained 1 ml of NaOH (1 M). Absorbance of the solution was determined at 450 nm.

One unit of protease activity is defined in the assay conditions, gives an increase of 0.001 absorbance unit at 450 nm per minute (Sarath et al., 1989).

The Effect of Organic Solvent on Protease Stability

Figure 3:
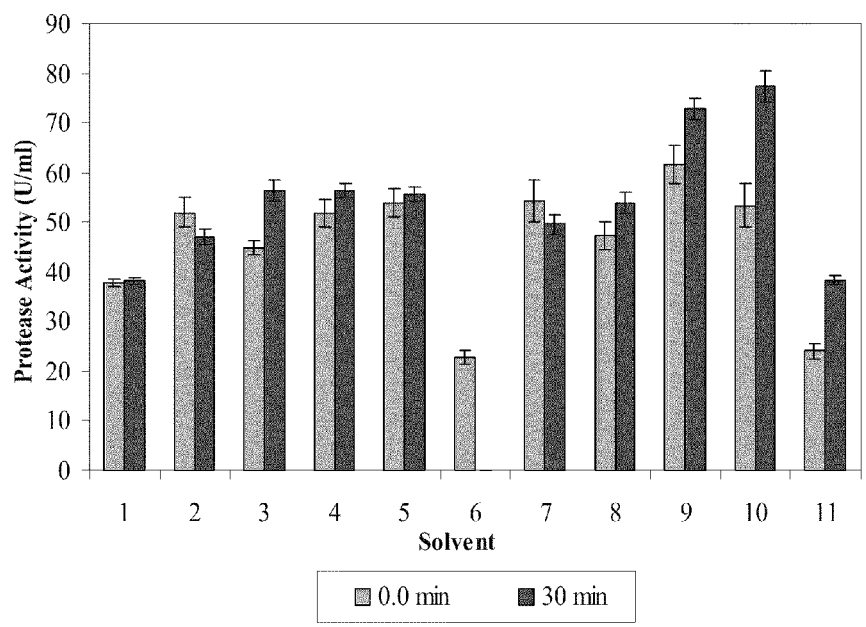
FIG. 3 shows Effect of organic solvent stability to isolate Rand. 1. Control 2. toluene (log P 2.5) 3. n-tetradecane (log P 7.6) 4. n-hexadecane (log P 8.8) 5. n-dodacane (log P 6.0) 6. pyridine (log P 0.71) 7. p-xylene (log P 3.1) 8. n-hexane (log P 3.5) 9. benzene (log P 2.0) 10. n-decane (log P 5.6) 11. butanol (log P 0.80). Three ml aliquots of a cell-free supernatant culture were incubated with 1 ml of different organic solvents at 55° C. with shaking at 150 rpm for 30 min.

The effects of various organic solvents 25% (v/v) with different log P values on protease stability were studied. Isolate Rand was cultured aerobically at 50° C. for 24 h in the absence of organic solvents. The culture medium was then centrifuged at 12,000×g and 4° C. for 10 min. The supernatant was filtered with a cellulose acetate membrane filter (pore size 0.22 μm). One mL organic solvent was added to 3.0 mL of the cell-free supernatant and the whole mixture was incubated in shaker 150 rpm at 55° C. for 30 min. The samples were removed and immediately vortex prior to assay at zero time and after incubation period. For control the solvent was replaced by distilled water. Protease activity was determined by a slight modification method of Rahman et al. (1994). Ten different organic solvents with different log p were used; toluene (log P 2.5), n-tetradecane (log P 7.6), n-hexadecane (log P 8.8), n-dodecane (log P 6.0), pyridine (log P 0.71), p-xylene (log P 3.1), n-hexane (log P 3.5), benzene (log P 2.0), n-decane (log P 5.6) and butanol (log P 0.80). All the solvents tested were found to enhance the enzyme activity except for pyridine (log P 0.71) whereby no activity was observed after the incubation period as shown in FIG. 3. On the contrary, benzene (log P 2.0) and n-decane (log P 5.6) showed high activity when compared to the control. The remaining activity of Rand protease was found to be 104, 197, 130, 134, 146, 209, 151, 152 and 151% in the presence of 25% (v/v) of butanol, benzene, toluene, p-xylene, n-hexane, n-decane, n-dodecane, n-tetradecane and n-hexadecane, respectively.

The Effect of Temperature on the Activity and Stability of Protease

Effect of temperature on protease activity was determined by using azocasein as the substrate. 100 μl of enzyme was added into each vial bottle containing 1 ml of substrate. Enzyme-substrate mixtures were incubated at various temperatures ranging from 40 to 80° C. for 30 min at 150 rpm in water bath shaker. The reaction was terminated by adding 1.1 ml of Trichloroacetic Acid (TCA) 10% (w/v) and allowed to stand at room temperature (25-27° C.) for 30 min. The precipitate protein was separated by centrifuging at 13000×g for 10 min. 1 ml of supernatant fluid was transferred into test tube contained 1 ml of NaOH (1 M). Absorbance of the solution was determined at 450 nm.

The effects of temperature on the protease stability were studied. The enzyme was incubated for 30 min at different temperature (37, 40, 45, 50, 55, 60, 65, 70° C.). After 30 min incubation samples were cooled rapidly in an ice bath. Protease activity was determined by a slight modification method from Rahman et al. (1994).

Figure 4:
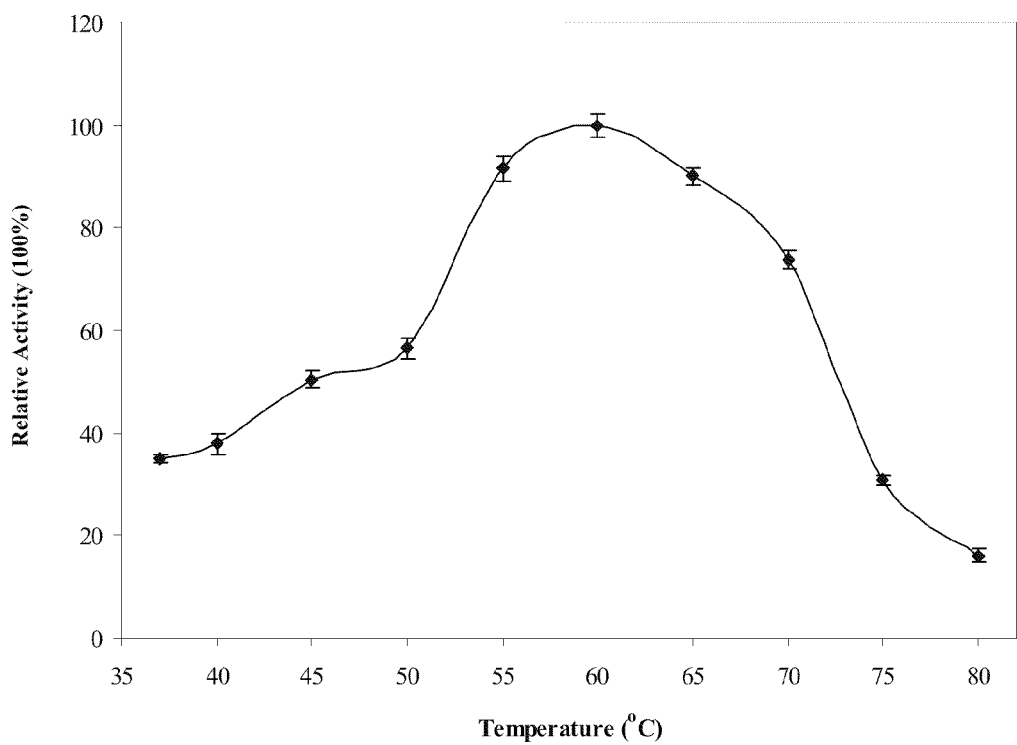
FIG. 4 shows Effect of temperature on protease activity. Rand protease was assay at different temperatures for 30 min. The activity at 60° C. was taken as 100%.
Figure 5:
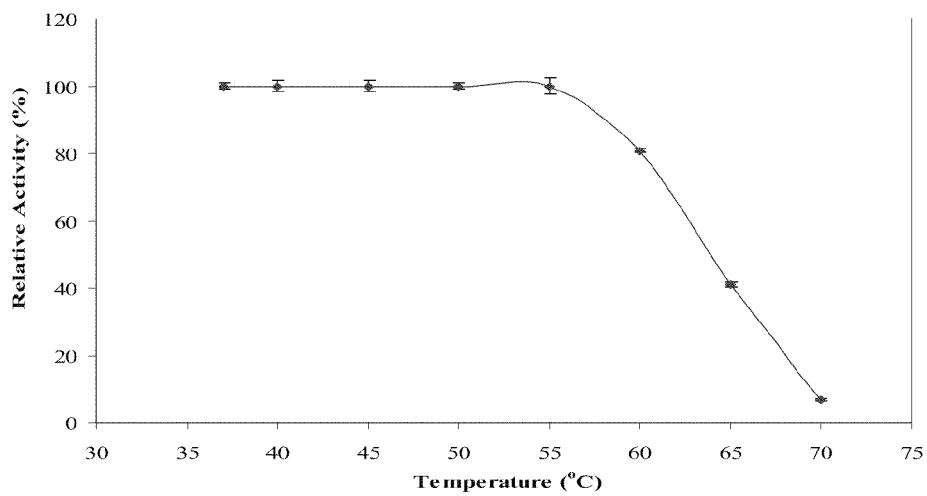
FIG. 5 shows Effect of temperature on protease stability. Rand protease was assay at different temperatures for 30 min. The activity at 37° C. was taken as 100%.

The optimum proteolytic activity of Rand protease was determined to be at 60° C. (348 U/ml) (FIG. 4). This Rand protease undergoes thermal activation above 37° C. with the maximum activity between 55 and 65° C. Then, the Protease activity was retained at about 70% of the activity even at 70° C. The protease appeared to be stable and retained its full activity after 30 min of incubation from 37 to 55° C. (FIG. 5). The crude enzyme retained 81% activity even after the heat treatment at 60° C. for 30 min. A reduction in the enzyme activity was observed at the temperature above 60° C. (FIG. 5).

Bacterial Identification
Genomic DNA Extraction

Genomic DNA extraction of *B. subtilis* isolate Rand was carried out by using the conventional method of Sambrook et al., (1989). Overnight isolate Rand culture was centrifuged at 15000×g for 10 min at 4° C. Pellet of bacterial cells was washed twice with 500 µl of GTE buffer [0.2% Glucose, 10 mM Tris-Cl, 1 mM EDTA, pH 8.0] and centrifuged at 14000×g for 10 min. The pellet was resuspended in 300 µl GTE buffer and kept in ice for 5 min. 20 µl of RNase and 50 µl of Lysozymes (10 mg/ml) were added and mixed gently. Then, the mixture was incubated in water bath at 37° C. for 2 hours. After incubation, 50 µl of proteinase K (1 mg/ml) and 50 µl of 25% (w/v) SDS were added and incubated at 50° C. for 30 min. The degraded proteins were removed by adding 500 µl of Phenol:Chloroform:Isoamyl alcohol (PCI) (v/v; 25:24:1). PCI was added and mixed gently by inverting the mixture for several times. The mixture was centrifuged at 14000×g for 15 min and two layers were formed. 400 µl of the upper layer was transferred into a new appendorf tube and the DNA was precipitated with 400 µl of sodium acetate (3.0 M, pH 5.5) and 800 µl of isopropanol. The mixture was incubated at room temperature (25-27° C.) for 10 min, and then centrifuged at 14000×g for 5 min. The DNA pellet was washed with 500 µl of 80% (v/v) ice cold ethanol followed by centrifuged at 14000×g for 10 min. The DNA pellet was air dried then dissolved in 50 µl of distilled water and stored at −20° C.

Amplification of 16S rDNA by Polymerase Chain Reaction (PCR)
Amplification of 16S rDNA by Polymerase Chain Reaction (PCR)

The 16S rDNA Sequence was amplified via the polymerase chain reaction (PCR) using two primers: forward 5'-GAGTTTGATCCTGGCTCAG-3' (SEQ ID NO: 2) and reverse 5'-CGGCTACCTTGTTACGACTT-3' (SEQ ID NO: 3). The polymerase chain reactions (PCR) were conducted by using genomic DNA as a template to amplified specific gene. The polymerase chain reaction was performed in 100 µl reaction mixture. The mixture containing genomic as template (10 ng/µl, 4.0 µl), 10×PCR buffer (10.0 ul), 25 mM MgC12 (6.0 ul), 10 mM deoxynucleotide triphosphatase (dNTP) mix (2.0 µl), forward primer (20 pmol, 2.0 µl) and reverse primer (20 pmol, 2.0 µl), Taq DNA polymerase (2.0 µl) and distilled water (72.0 µl). The reactions were carried out for 30 cycles, each cycle with 4 min predenaturation at 94° C., 1 min denaturation at 94° C., 2 min annealing at specific temperature based on melting temperature (Tm) of primers, 2 min extension at 72° C. and the final 7 min elongation step at 72° C. for one cycle. The PCR was carried out in GeneAmp PCR system 9600 (Perkin-Elmer). The amplified products were electrophoresed on agarose gel.

Agarose Gel Electrophoresis

Agarose gel electrophoresis was performed with horizontal gel. 1% (w/v) of agarose was dissolved in 1×Tris-Acetate-EDTA buffer (TAE) and poured into the gel mold to make the horizontal gels. The ingredient of 50×TAE buffer stock were 242 g of Tris, 57.1 ml acetic acid, 100 ml of 0.5 M EDTA (pH 8.0) and the volume was adjusted to 1 L with $dH_2O$. A comb was hanged into the agarose to form wells. After the agarose solidifies, the comb was removed and the gel was placed in container with 1×TAE buffer covering the gel. A mixture of 3 µl loading dye and 5 µl PCR product was transferred into agarose gel well. DNA size marker was loaded into another well. The electrophoresis container was connected to the power supply and electrophoresed under a constant voltage at 80 mA for approximately 35 min and then the electrophoresed gel was stained in ethidium bromide (0.5 µg/ml) in $dH_2O$ for 15 min. The gel was placed on UV transilluminator and visualized under UV light.

Purification of the PCR Product

PCR products were purified by agarose gel electrophoresis. 100 µl of PCR product was added and mixed with 10 µl of loading dye (6×). The mixtures were loaded into well of agarose gel and electrophoresed at 60 mA for approximately 1 hour and 30 min, then stained with ethidium bromide (0.5 µg/ml). Under UV light, the desired fragments were cut with sterile blade and transferred into sterile appendorf tube. The samples of PCR products were extracted from agarose gel by using QIAquick Gel Extraction Kit (QIAGEN, Germany) according to the manufacture's instruction. The purified product was send to First BASE laboratories Sdn Bhn (Shah Alam, Selangor, Malaysia) for sequencing. DNA homology search on the GenBank database (www.ncbi.nih.gov) was performed.

Figure 6:
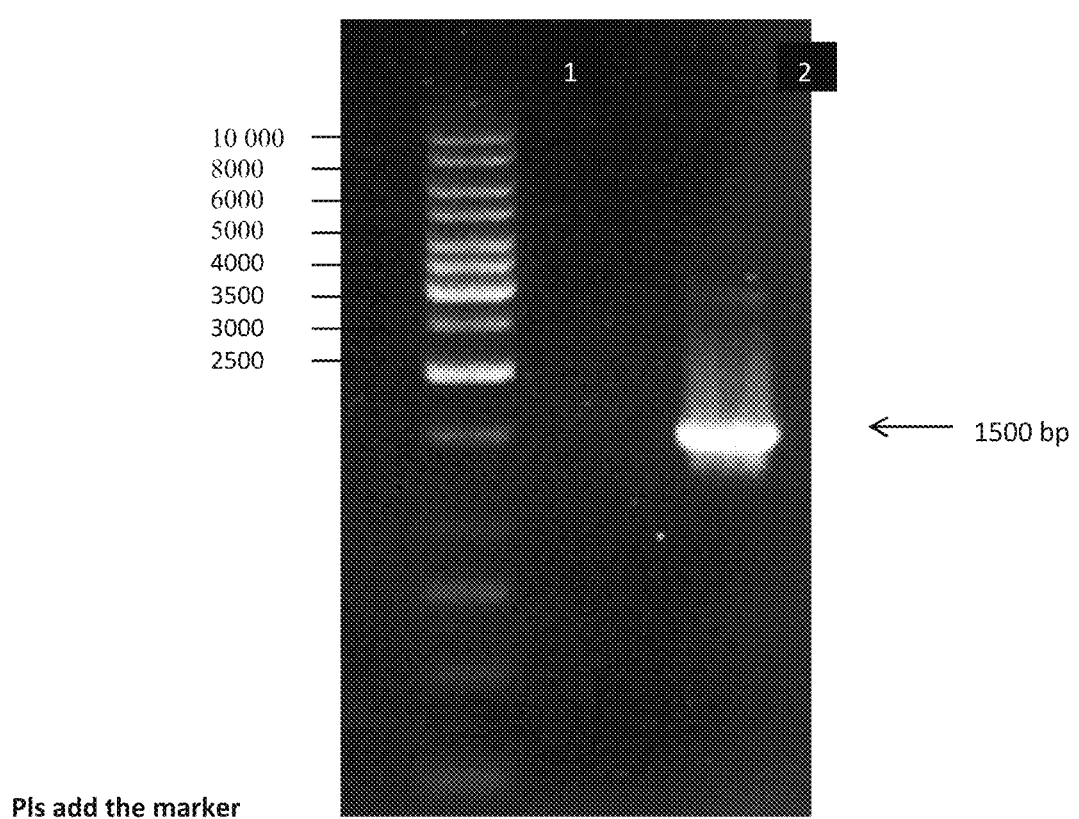
FIG. 6 shows amplified of 16S rRNA PCR product. Lane 1: Marker GeneRuler DNA 1 kb Lane 2: PCR product of amplified 16S gene.

The rRNA gene of isolate Rand which was 1458 bp (FIG. 6) was purified and sequenced (FIG. 7). The partial sequencing of the 16S rDNA shows a 99.6% similarity to the different strains of *Bacillus subtilis*. The analysis of the cellular fatty acids indicated a good correspondence to the profile of the *Bacillus subtilis* group.

Phylogenetic Tree Analysis

Figure 8:
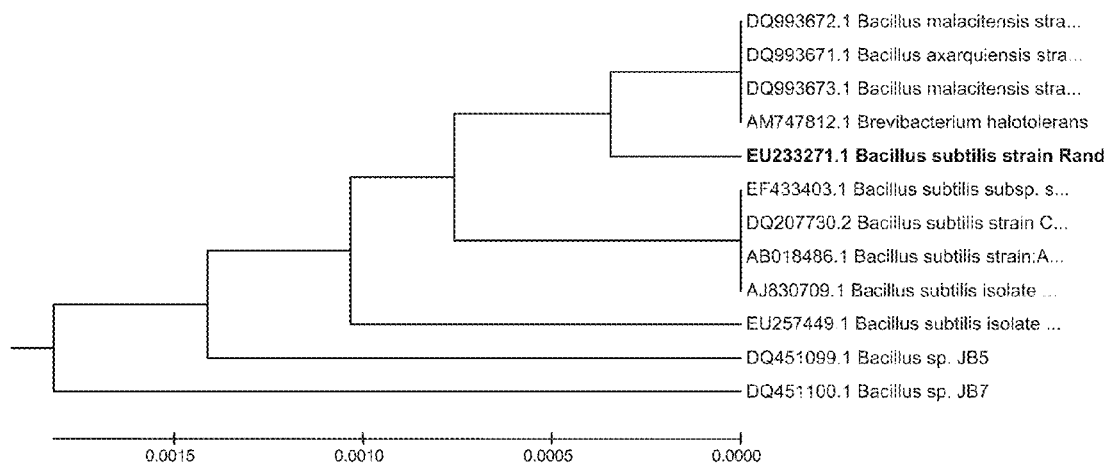
FIG. 8 shows phylogenetic position of isolate Rand with other bacteria. The phylogenetic tree including *Bacillus malacitensis* CECT 5687; *Bacillus axarquiensis* LMG 22476; *Bacillus malacintesis* LMG 22477; *Brevibacterium halotolerans*; *Bacillus subtilis* subsp. *spizizenii* BCRC 10447; *Bacillus subtilis* CCM 1999; *Bacillus subtilis* AU30; *Bacillus subtilis* isolate KCM-RG5; *Bacillus subtilis* isolate C10-1. Phylogenetic tree was inferred by using the neighbour-joining methods. The software package MEGA 4 was used for analysis.

A phylogenetic tree was constructed based on comparison of the 16S rDNA sequence of isolate Rand with other strains. All sequences were aligned with CLUSTALW from Biology WorkBench database at (workbench.sdsc.edu) (Thompson et al., 1994). The 16S rDNA sequence of *Bacillus subtilis* isolate Rand was analyzed using software package MEGA 4 (Tamura et al., 2007). FIG. 8 shows the phylogenetic tree including *Bacillus malacitensis* CECT 5687; *Bacillus axarquiensis* LMG 22476; *Bacillus malacintesis* LMG 22477; *Brevibacterium halotolerans*; *Bacillus subtilis* subsp. *spizizenii* BCRC 10447; *Bacillus subtilis* CCM 1999; *Bacillus subtilis* AU30; *Bacillus subtilis* isolate KCM-RG5; *Bacillus subtilis* isolate C10-1. Phylogenetic tree was inferred by using the neighbor-joining methods. The software package MEGA 4 was used for analysis.

Morphological and Biochemical Characteristics

Morphological and physiological characteristics were further determined at Deutsche Sammlung Von Mikroorganismen (DSMZ), Germany. The physiological characteristics study included catalase and oxidase test, anaerobic growth, Voges-Proskauer test, growth at 30, 50 and 55° C., growth in medium at pH 5.7, 2%, 5%, 7% and 10% NaCl, fermentation of D-glucose, L-arabinose, D-xylose, D-mannitol, D-fructose, hydrolysis starch, gelatin, casein and Tween 80, use of citrate and propionate, nitrate reduction, indole production, phenylalanine deaminase and arginine dihydrolase test.

Isolate Rand was an aerobic, rod-shaped with 0.7-0.8 μm in width and 2.5-3.0 μm in length, Gram positive bacteria. The biochemical, morphological and physiological properties of the isolate Rand are listed in Table 2. The isolate Rand could be grown at 50° C., pH 5.7 and 10% NaCl. It is able to ferment D-glucose, L-arabinose, D-xylose, D-mannitol and D-fructose. In addition, it can also use citrate and has the capability to reduce nitrate. Isolate Rand could hydrolyse starch, gelatin, casein and Tween 80 and propionate.

The genus *Bacillus* constitutes a diverse group of rod-shaped, Gram-positive aerobic or facultative bacteria which are characterized by their ability to produce robust endospores in response to the adverse environmental conditions (Slepecky, 1992). According to 16S rDNA analysis, the biochemical results and morphological properties, the bacterium was identified as *Bacillus subtilis* isolate Rand. *Bacillus* species of industrial importance are vastly applied in the production of several biological products. These species are important organisms for both fundamental research and industrial applications (Schmidt, 2004).

TABLE 2

Morphological and biochemical characteristics of *B. subtilis* isolate Rand

| Characteristics | Isolate Rand results |
|---|---|
| Rods | + |
| Width μm | 0.7-0.8 |
| Length μm | 2.5-3.0 |
| Aminopeptidase test | − |
| KOH test | − |
| Oxidase | + |
| Catalase | + |
| Gram stain | + |
| Spores | + |
| Sporangium swollen | − |
| Anaerobic growth | − |
| VP reaction | + |
| pH in VP broth | 5.5 |
| Growth positive at | 50° C. |
| Growth negative at | 55° C. |
| Medium pH 5.7 | + |
| NaCl 10% | + |
| D-glucose | + |
| L-arabinose | + |
| D-xylose | + |
| D-mannitol | + |
| D-fructose | + |
| Use of citrate | + |
| Use of propionate | − |
| $NO_2$ from $NO_3$ | + |
| Indol reaction | − |
| Phenylalanine deaminase | − |
| Arginine dihydrolase | − |
| Hydrolysis of starch, gelatin, casein and tween 80 | + |

Growth Curve and Protease Production by *Bacillus subtilis* Isolate Rand

Figure 9:
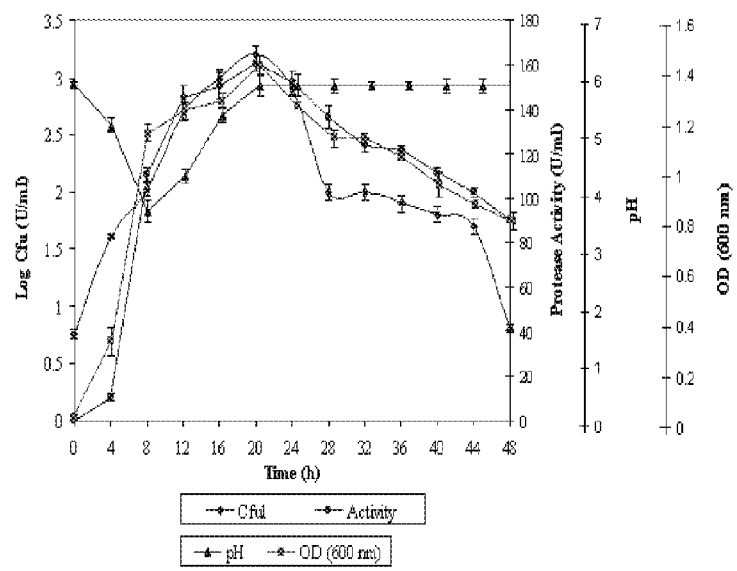
FIG. 9 shows growth curve and protease production by *B. subtilis* isolate Rand. The growth and protease production were investigated in M2 at 37° C. and 150 rpm for 48 h. Samples were withdrawn at 4 h intervals.

A loop-full of 24 h-old single colony of isolate Rand was transferred from a fresh Nutrient agar plate into 10 ml tryptone soy broth in universal bottle and incubated in shaker (150 rpm) at 50° C. overnight. The cells were harvested by centrifugation at 12,000×g for 10 min and the bacterial pellets were dissolved in physiological saline 0.85% (w/v) NaCl to give an absorbance reading of ($AB_{600}$=0.5). Inoculum size at $AB_{600}$=0.5, 5% (v/v) of the isolate 1 L screw cab media-lab bottle of medium (M2) (pH 7.0) and incubated at 37° C. (optimum temperature for *B. subtilis* growth) and 150 rpm on shaker for 48 hours. Samples were taken at 4 h intervals for 48 h to measure the protease production, pH of the culture medium, bacterial count and bacterial optical density. Samples were diluted in dilution tubes of 0.85% NaCl and inoculated on plates by spread plate technique. The cell densities were determined spectrophotometrically by reading the optical densities at 600 nm absorbance. FIG. 9 determines growth and protease production were investigated in M2 at 37° C. and 150 rpm for 48 h. Samples were withdrawn at 4 h intervals.

The Effect of Physical Factors on the Protease Production
The Effect of Temperature on the Production of Protease Temperature is an important environmental factor affecting the growth and production of protease by micro-organisms. The ability of *Bacillus subtilis* isolate Rand to grow and produced protease at elevated temperatures (30 to 65° C.). Inoculum size at $AB_{600}$=0.5, 5% (v/v) of isolate Rand was inoculated into 500 mL screw cab media-lab bottles of 50 mL M2 medium. Separate cultures were incubated at 30, 37, 40, 45, 50, 55, 60 and 65° C. for 24 h with agitation at 150 rpm. Protease activity was determined by a slight modification method of Rahman et al. (1994).

Figure 10:
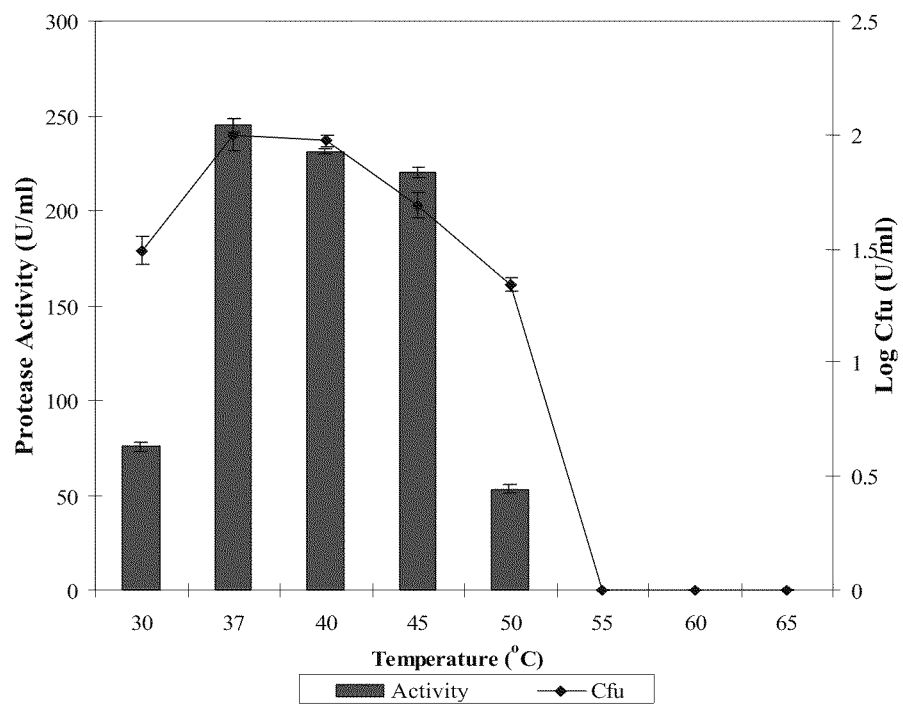
FIG. 10 shows effect of temperature on protease production and bacterial growth. Culture media were incubated at 30, 37, 40, 45, 50, 55, 60 and 65° C. with shaking at 150 rpm for 24 h.

FIG. 10 represents Culture media were incubated at 30, 37, 40, 45, 50, 55, 60 and 65° C. with shaking at 150 rpm for 24 h.

The Effect of pH on the Protease Production

The effect of pH on the growth and protease production was studied by adjusting the media to different pH from pH 4 to 13. Inoculum size at $AB_{600}$=0.5, 5% (v/v) of isolate Rand was inoculated into 500 mL screw cab media-lab bottles of 50 mL M2 medium, the pHs were adjusted by (1 M) NaOH and (1 M) HCl. Separate cultures were incubated at 37° C. (optimum temperature for protease production) for 24 h under 150 rpm agitation in shaker. Protease activity was determined by a slight modification method of Rahman et al. (1994).

Figure 11:
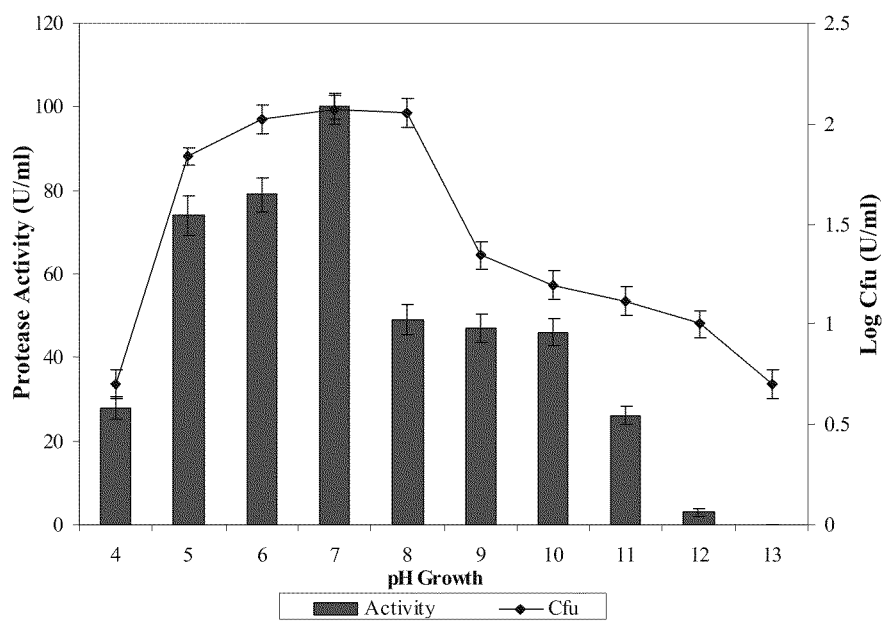
FIG. 11 shows effect of pH on protease production and bacterial growth. Bacterial cultures were adjusted to pH 4, 5.0, 6.0, 7.0, 8.0, 9.0, 10.0, 11.0, 12.0 and 13.0 incubated at 37° C. with 150 rpm shaking condition for 24 h.

The pH of the basal medium had a profound effect on the bacterial growth and the production of protease by isolate Rand. Extra-cellular protease was detected over a broad pH range (i.e. pH 4.0 to pH 11.0), with the optimum growth and protease production exhibited at pH 7.0 (FIG. 11). The production of protease in an acidic medium at pH 6.0 was found to be higher as compared to that in the alkaline pH 8.0, while no activity was observed at pH 13.0. However, at extreme acidity of pH 4.0, the production of protease was greatly reduced (FIG. 11).

The Effect of Agitation Rate on the Protease Production

The effect of agitation rate on growth and protease production was studied by cultivating the bacteria under different agitation rate (0 to 250 rpm). The media were adjusted to pH 7.0 (optimum pH for protease production). Inoculum size at $AB_{600}$=0.5, 5% (v/v) of isolate Rand was inoculated into 500 mL screw cab media-lab bottles of 50 mL M2 medium. Separate cultures were incubated at 37° C. for 24 h. Protease activity was determined by a slight modification method of Rahman et al. (1994).

Figure 12:
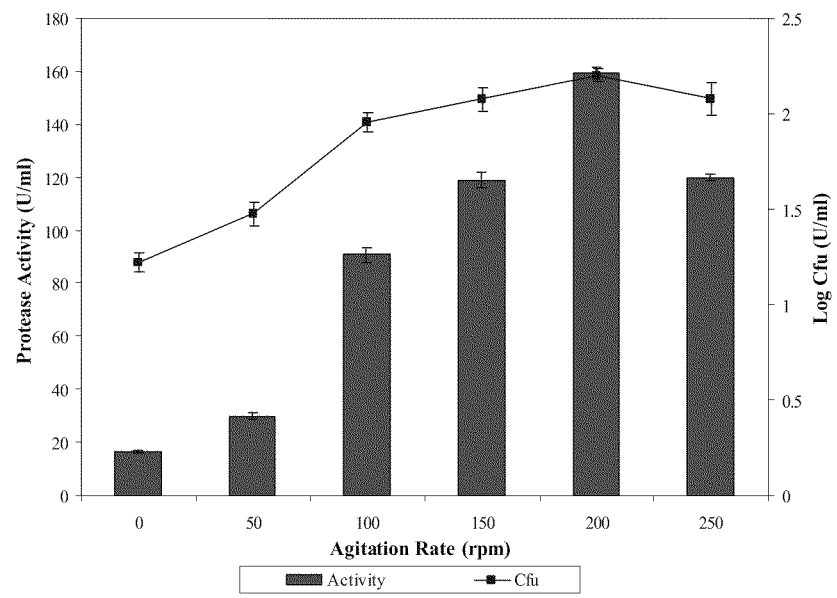
FIG. 12 shows effect of agitation rate on protease production and bacterial growth. Culture media were incubated at 37° C. with different shaking rates (0, 50, 100, 150, 200 and 250 rpm) for 24 h.

The highest growth and protease production were obtained when agitation was done at 200 rpm. The production of protease was found to decrease when shaken at 250 rpm, while the lowest protease production was revealed at static incubation (FIG. 12).

The Effect of Inoculum Size on the Protease Production

Figure 13:
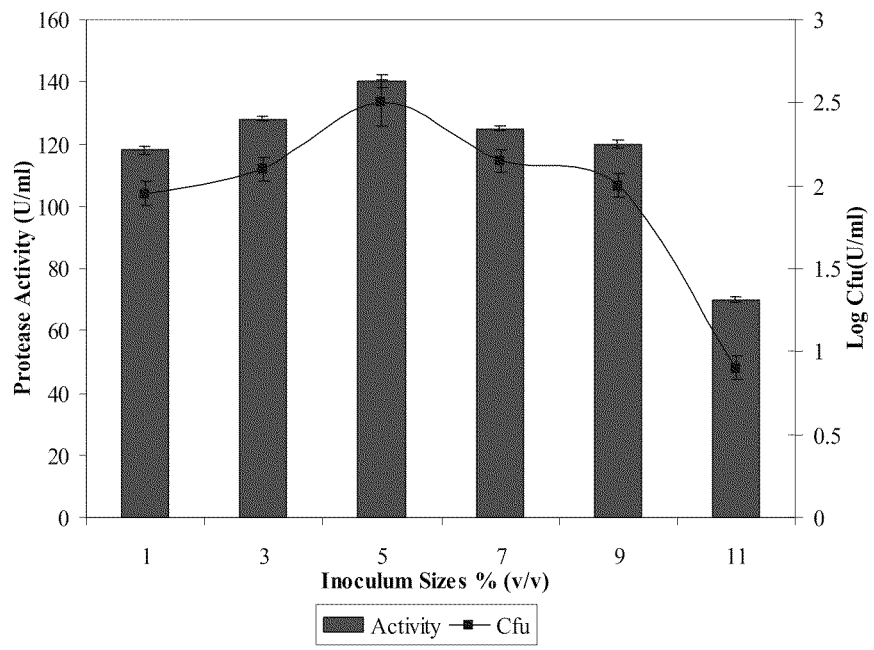
FIG. 13 shows effect of inoculum size on protease production and bacterial growth. Culture media were incubated with 1.0%, 3.0%, 5.0%, 7.0%, 9.0%, 11.0% (v/v) of inoculum and incubated at 37° C. with shaking at 200 rpm for 24 h.

The effect of inoculum size ($A_{600}$=0.5) on growth and protease production was investigated by using different inoculum size ranging from 1% to 11%. The cultures were incubated at 37° C. for 24 h under agitation rate 200 rpm (optimum agitation rate for protease production). Protease activity was determined by a slight modification method of Rahman et al. (1994). Protease production was achieved with an inoculum size of 5% (v/v), as shown in FIG. 13. The increase in the production of protease using small inoculum sizes was suggested to be due to the higher surface area to volume ratio resulting in the increased protease.

The Effect of Medium Volume on the Protease Production

Figure 14:
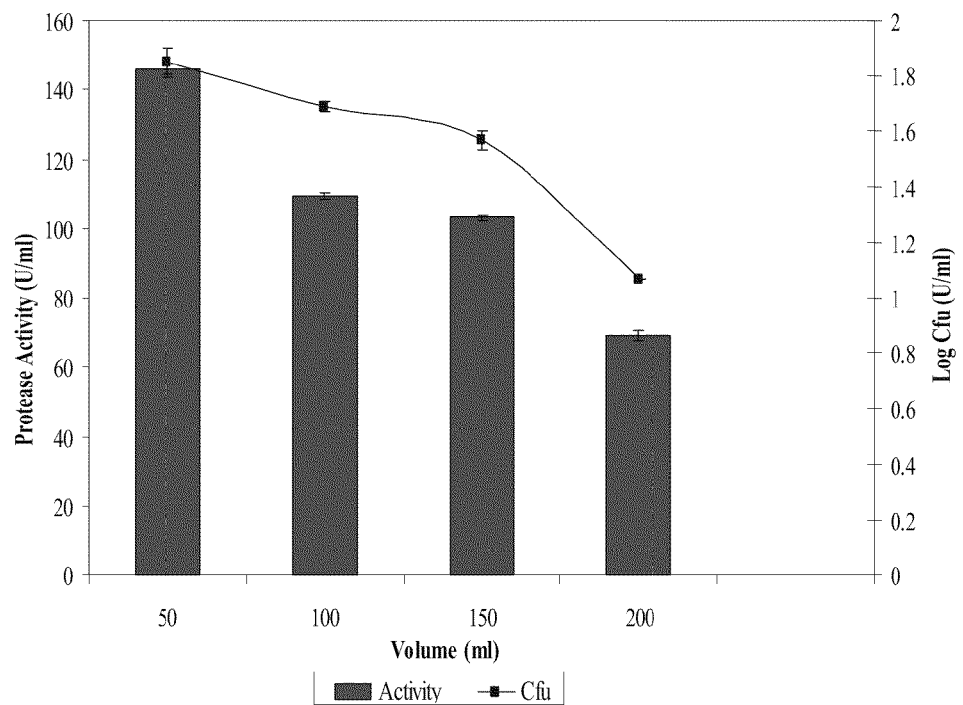
FIG. 14 shows effect of medium volume on protease production and bacterial growth. Different media volume was incubated with 5.0% (v/v) of inoculum at 37° C. with shaking at 200 rpm for 24 h.

The effect of medium volume on growth and protease production was investigated by cultivating the bacterium on different volumes of medium 50, 100, 150 and 200 mL in standard 500 mL screw cab media-lab bottles. The media were adjusted to pH 7.0 and incubated at 37° C. for 24 h under agitation rate 200 rpm. Protease activity was assayed according to the modified method of Rahman et al. (1994). The effects of the medium volume on the growth of bacteria and the production of protease by isolate Rand are shown in FIG. 14. The highest production of protease and the best bacterial growth were obtained from 50 mL medium (FIG. 14). This volume with its void supplied the most oxygen for the maximum protease production. On the other hand, a volume of 200 mL was found to decrease the production of protease too much (FIG. 14). Meanwhile, as a larger volume contains more food and nutrients, the void in the container is therefore decreased. The lower protease production is believed to be largely caused by the smaller void and the consequent poorer aeration.

The Effect of Nutritional Factors on the Protease Production

The Effect of Carbon Sources on the Protease Production

Figure 15:
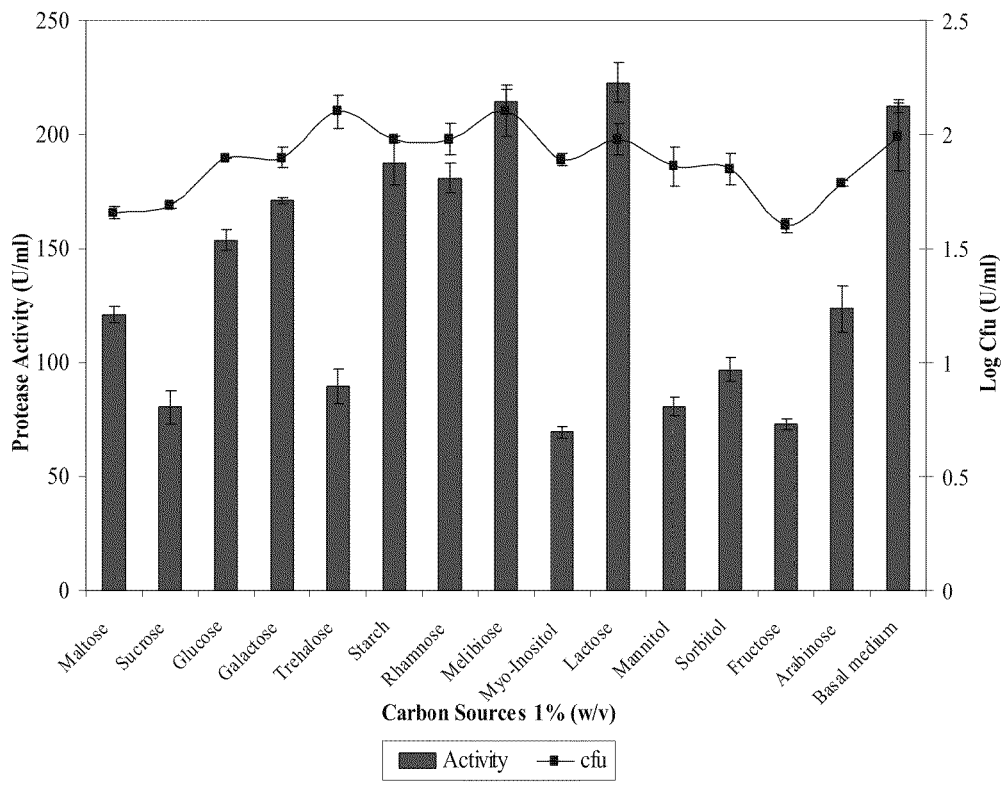
FIG. 15 shows effect of carbon sources on protease production and bacterial growth. The bacterial growth and extracellular protease activity were determined after 24 h incubation at 37° C. and an initial pH 7.0

The effects of carbon source 1% (w/v) on growth and protease production by isolate Rand was assessed with the addition of various carbon sources to the basal medium. The carbon sources added were maltose, sucrose, glucose, galactose, trehalose, starch, rhamnose melibiose, myo-inositol, lactose, mannitol, sorbitol, fructose and arabinose, respectively. Each source was dissolve in water to a concentration of 25% (w/v) and then sterile filtered through a 0.22 µm membrane filter. The sterilized carbon sources were then added to the media to a final concentration of 1%. The media were dispensed in 50 ml batches into 500 mL screw cap media-lab bottle. The initial pH of the media was adjusted to 7.0, and the cultures incubated at 37° C. for 24 h with 200 rpm agitation in a shaker. Protease activity was determined by a slight modification method of Rahman et al. (1994). The ability of the isolate Rand to utilize various carbon sources to produce protease is shown in FIG. 15. All the carbon sources were indicated to decrease the production of protease, and only lactose and melibiose were found to improve its protease production.

The Effect of Inorganic Nitrogen Sources on the Protease Production

Figure 16:
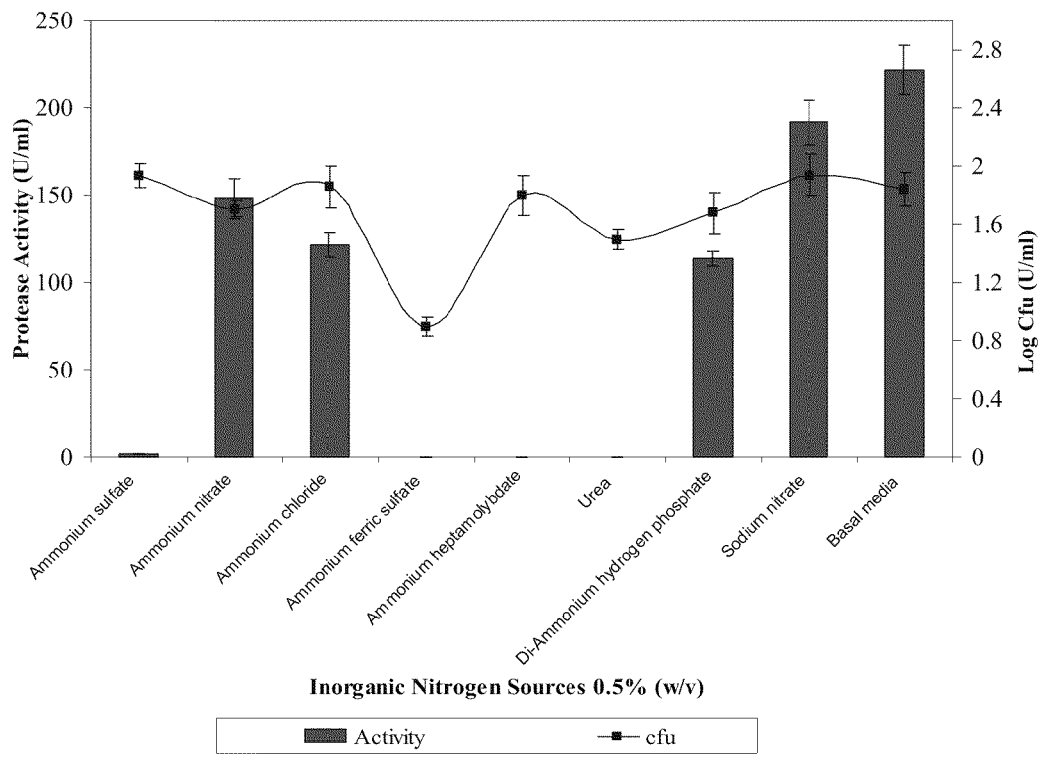
FIG. 16 shows effect of inorganic nitrogen source on protease production and bacterial growth. The bacterial growth and extracellular protease activity were determined after 24 h incubation at 37° C. and an initial pH 7.0

Various inorganic nitrogen sources were tested such as ammonium sulfate, ammonium nitrate, ammonium chloride, ammonium ferric sulfate, ammonium heptamolybdate, urea, di-ammonium hydrogen phosphate and sodium nitrate, respectively. The nitrogen sources were added to a final concentration of 0.5% (w/v). The pH of each the medium was adjusted to 7.0 and the cultures incubated at 37° C. for 24 h with 200 rpm agitation in a shaker. Protease activity was determined by a slight modification method of Rahman et al. (1994). The effects of some inorganic nitrogen sources on the growth and the production of protease by *B. subtilis* isolate Rand were studied (FIG. 16). All the inorganic nitrogen sources used supported the bacterial growth.

The Effect of Organic Nitrogen Sources on the Protease Production

Figure 17:
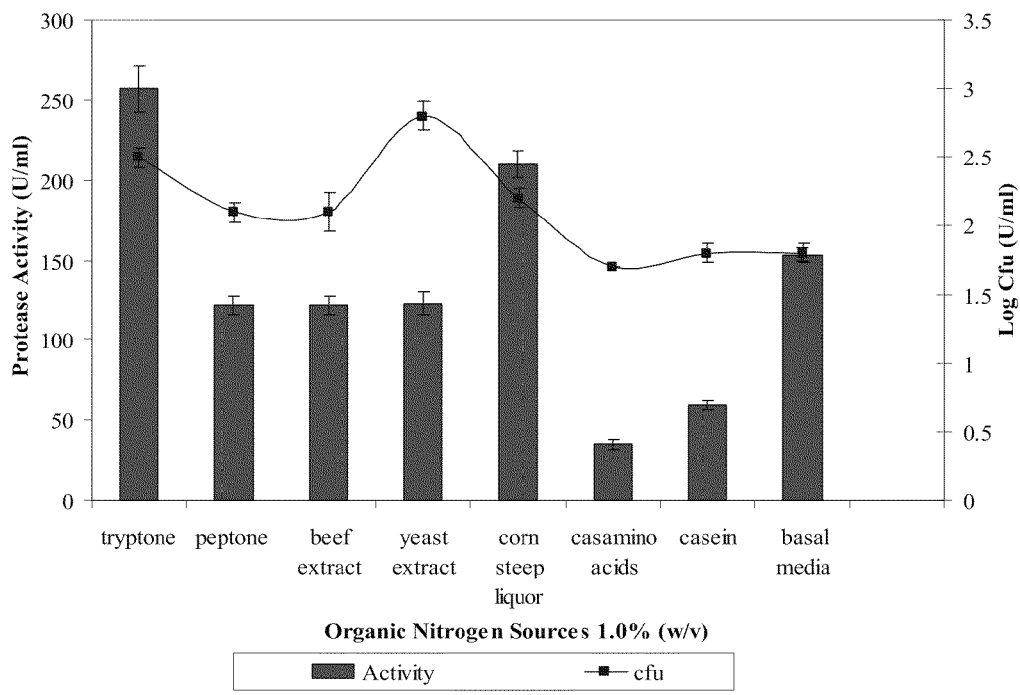
FIG. 17 shows effect of organic nitrogen on protease production and bacterial growth. The bacterial growth and extracellular protease activity were determined after 24 h incubation at 37° C. and an initial pH 7.0

The effect of organic nitrogen sources on growth and protease production was examined using various organic substances as nitrogen sources—casein, casamino acid, yeast extract, tryptone, peptone, beef extract, protease peptone and corn steep liquor. The nitrogen sources were added to a final concentration of 1.0% (w/v). The pH of each the medium was adjusted to 7.0 and the cultures incubated at 37° C. for 24 h with 200 rpm agitation in a shaker. In this study peptone, type iv was eliminated from the basal media (M2). Protease activity was determined by a slight modification method of Rahman et al. (1994). All the organic nitrogen sources tested supported a good bacterial growth although the enzyme production differed greatly between the sources, with some give a very poor production (FIG. 17). The highest production of protease was obtained with tryptone, and this supported a good bacterial growth as well.

The Effect of Amino Acids on the Protease Production

Figure 18:
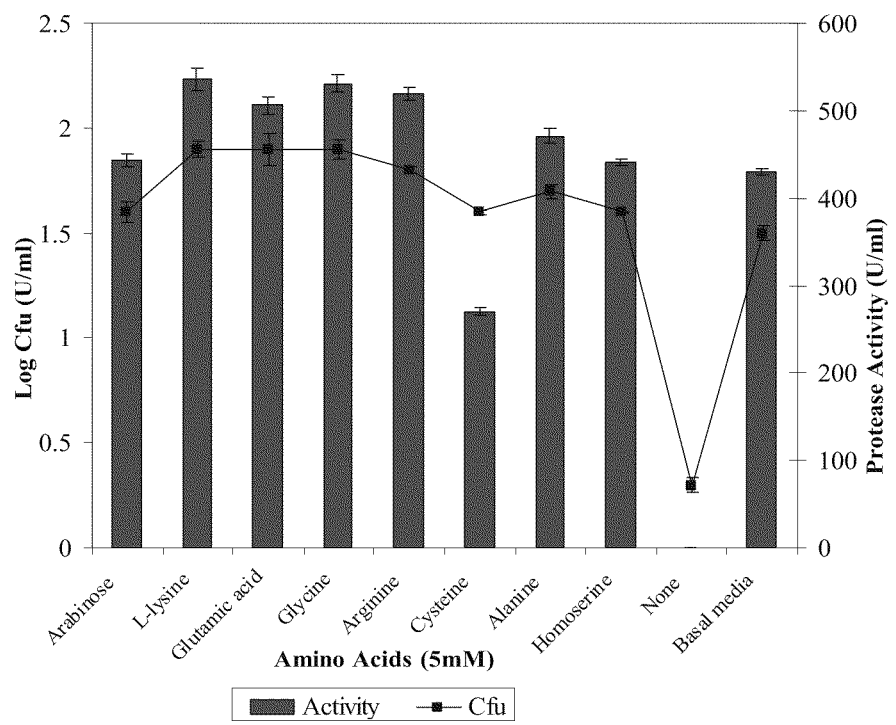
FIG. 18 shows effect of amino acids on protease production and bacterial growth. The bacterial growth and extracellular protease activity were determined after 24 h incubation at 37° C. and an initial pH 7.0. None is the basal media without amino acids and tryptone.

The effect of amino acids on growth and protease production was carried out by adding 5 mM of amino acids directly into the basal medium. The amino acids added were L-lysine, glutamic acid, glycin, arginine, cysteine, alanine, arabinose and homoserine. The pH of each the medium was adjusted to 7.0 and the cultures incubated at 37° C. for 24 h with 200 rpm agitation in a shaker. In this study peptone, type iv was eliminated from the basal media (M2). Protease activity was determined by a slight modification method of Rahman et al. (1994). Lysine, glycine arginine, glutamic acid, alanine, arabinose and homoserine enhanced the bacterial growth and protease production (FIG. 18). In the presence of lysine and glycine, both the bacterial growth and the production of protease were observed to be high. Cysteine, on the other hand, did not increase the production of protease and the bacterial growth was found to remain high. No protease production was observed when treptone and amino acids were eliminated from the basal media.

The Effect of Metal Ions on the Protease Production in the Basal Media

Figure 19:
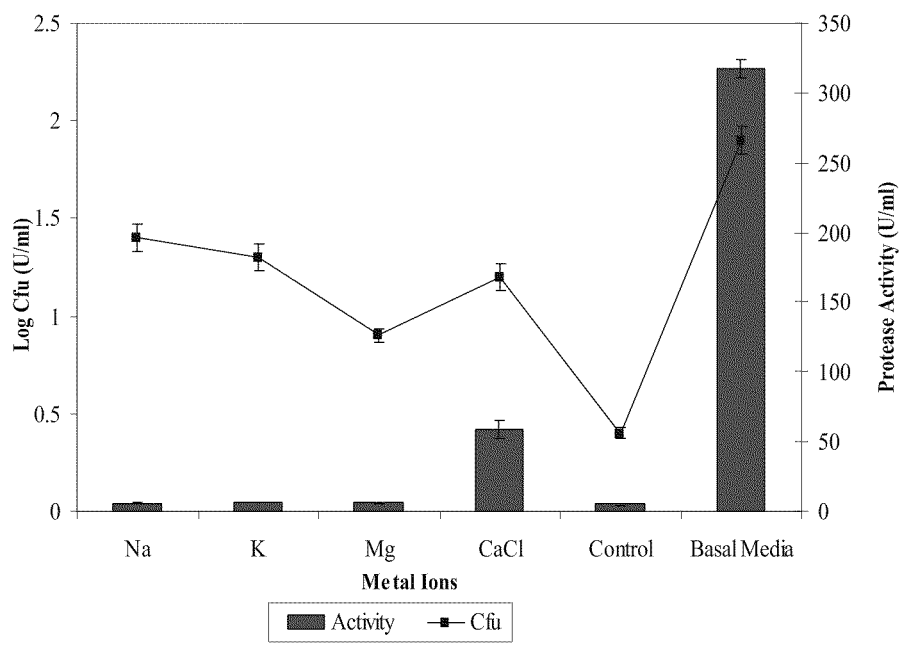
FIG. 19 shows optimization of metal ions on the basal media and bacterial growth. The bacterial growth and extracellular protease activity were determined after 24 h incubation at 37° C. and an initial pH 7.0
Figure 20:
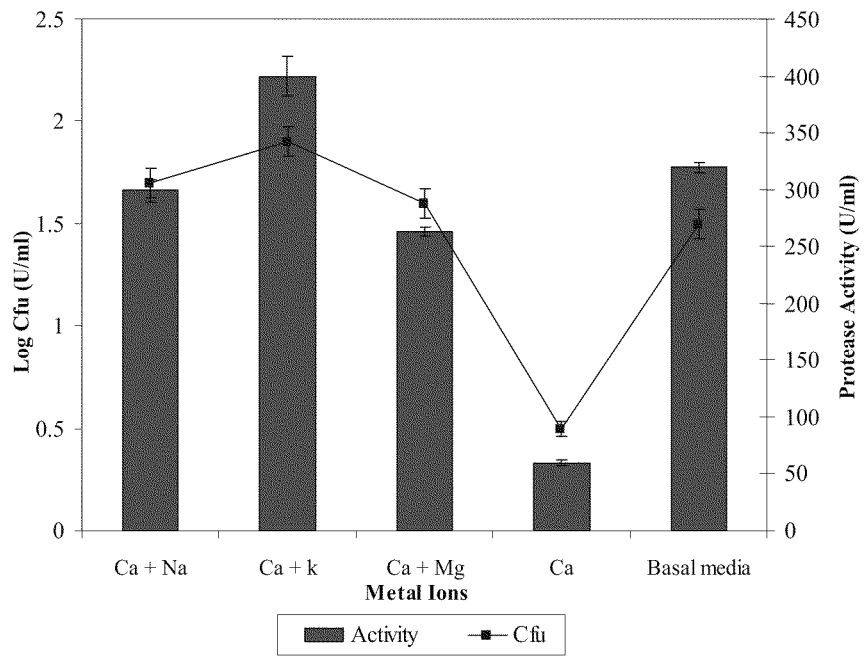
FIG. 20 shows optimization of metal ions on the basal media and bacterial growth. The bacterial growth and extracellular protease activity were determined after 24 h incubation at 37° C. and an initial pH 7.0

To investigate the effects of metal ions on growth and protease production by isolate Rand, $Na^{+1}$, $K^{+1}$, $Mg^{+2}$ and $Ca^{+2}$ from sodium chloride, potassium dihydrogen phosphate, magnesium sulphate and calcium chloride were tested individually at the original concentration (0.01%, 0.02%, 0.05% and 0.05%) in the basal medium. Each one of $Na^{+1}$, $K^{+1}$ and $Mg^{+2}$ were added with $Ca^{+2}$ into the basal medium. The initial pH of the media was adjusted to 7.0, and the cultures incubated at 37° C. for 24 h with 200 rpm agitation in a shaker. Protease activity was determined by a slight modification method of Rahman et al. (1994). FIG. 19 represents Optimization of metal ions on the basal media and bacterial growth. Production of the Rand protease was lower with the combinations of $Ca^{2+}+Mg^{2+}$ and $Ca^{2+}+Na^+$ (FIG. 20). The protease activity and bacterial growth were stimulated by a combination of $Ca^{2+}+K^+$.

The Effect of Additional Metal Ions on the Protease Production

Figure 21:
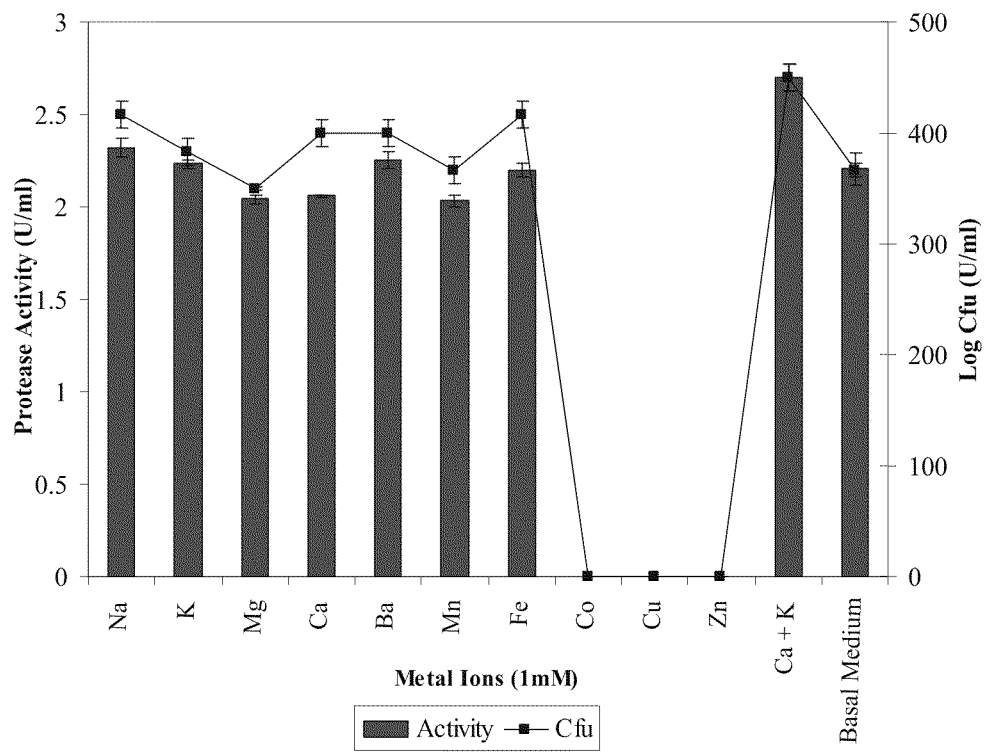
FIG. 21 shows effect of additional metal ions on protease production and bacterial growth. The bacterial growth and extracellular protease activity were determined after 24 h incubation at 37° C. and an initial pH 7.0

Various metal ions were studied such as sodium chloride, potassium dihydrogen phosphate, magnesium sulphate, calcium chloride, manganese chloride, ferric chloride, cobalt chloride, copper chloride, zinc chloride and barium chloride respectively. Each metal ions at 1 mM were added to the basal medium. The pH of each the medium was adjusted to 7.0 and the cultures incubated at 37° C. for 24 h with 200 rpm agitation in a shaker. Protease activity was determined by a slight modification method of Rahman et al. (1994). Among all the different metal ions tested, only $Ba^{2+}$, $Na^+$, $Fe^{2+}$ and $K^+$ were found to be enhancing the production of protease by the isolate Rand (FIG. 21). All the additional metal ions were found to enhance bacterial growth except for $Cu^{2+}$, $Co^{2+}$ and $Zn^{2+}$ which resulted in no bacterial growth. The highest bacterial growth and protease activity were observed when the medium containing the combination of $Ca^{2+}$ and $K^+$ was used. However, a stronger inhibitory effect was observed in the presence of $Cu^{2+}$, $Co^{2+}$ and $Zn^{2+}$ resulted in the complete loss of protease activity. Protease activity was stimulated by $K^+$ and Ca+, indicating that these ions had a functional role in the molecular structure of the enzyme.

Purification of Protease

Most purification protocols require more than one step to achieve the desired purity level of a product. However, it is important to reach the target for the yield and purity with the minimum numbers of step. The purification of protease from Bacillus subtilis isolate Rand was carried out on 2 steps.

Crude Enzyme Preparation for Purification

Culture preparation was done according to the optimum production of protease condition. A single colony of Bacillus subtilis isolate Rand from the overnight was inoculated into 10 ml of TSB. The culture was incubated overnight at 37° C. with agitation rate at 200 rpm. 2.5 ml bacterial culture of $A_{600}=0.5$ was inoculated into a 500 mL screw cab media-lab bottle containing 50 ml of the production medium. The culture was then incubated overnight at 37° C. under shaking rate at 200 rpm for 20 h. The culture was centrifuged at 15000×g at 4° C. for 30 min. The centrifuged supernatant was filtered through 0.22 μm cellulose acetate filter, and kept in ice for the next step. The supernatant was analyzed for protease activity and protein content.

Hydrophobic Interaction Chromatography (HIC)

Figure 22:
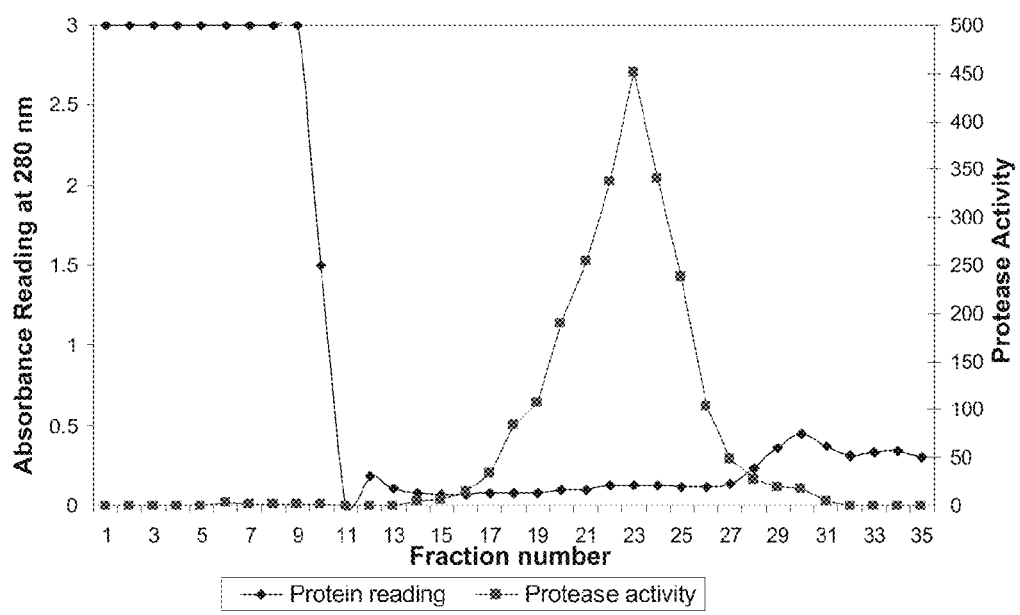
FIG. 22 shows purification profile of Rand protease on Octyl-Sepharose chromatography.

Octyl-Sepharose fast flow media was used in hydrophobic interaction chromatography. Column was packed with 5 ml hydrophobic media. Phosphate buffer (50 mM, pH 7.0) containing $NH_2SO_4$ (1.4 M) was used as binding buffer. The column was equilibrated with 2 column volume of binding buffer. 50 ml of active crude enzyme was applied directly to the column at flow rate of 1 ml/min (2.98 cm/h). Five column volume of binding buffer were run through the column in washing step. The bound proteins to the hydrophobic gel were eluted by descending linear gradient of the $NH_2SO_4$ concentration from 1.4 to 0 M of $NH_2SO_4$ in 50 mM Phosphate buffer and 40% isoporpanol (pH 7.0). Volume of 2.5 ml was collected for each fraction. Each fraction was assay for protease activity, protein concentration, and SDS PAGE electrophoresis. The active protease fractions were pooled together and kept at 4° C. The Rand protease was eluted at the concentration of $NH_2SO_4$, starting from 0.56 M to 0.26 M (FIG. 22).

Figure 23:
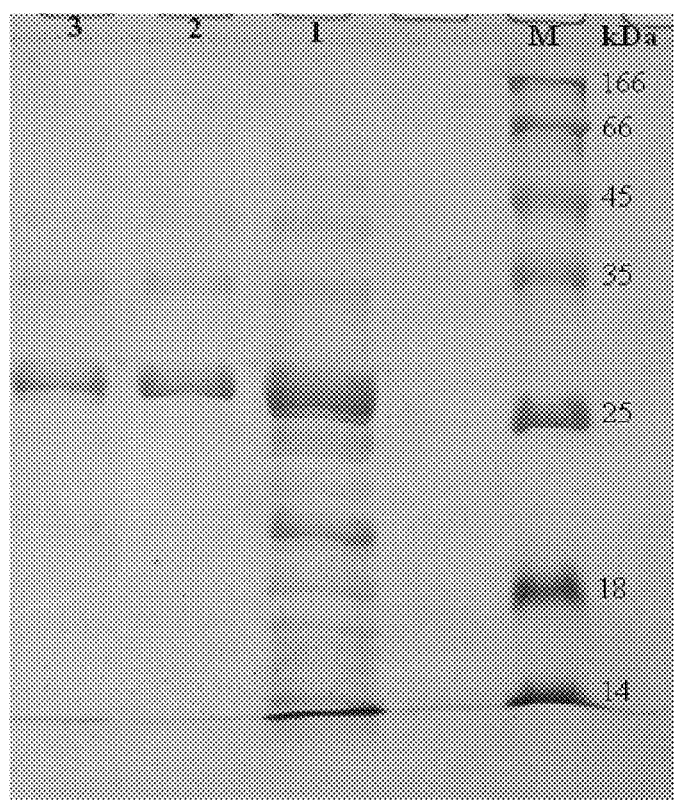
FIG. 23 shows SDS-PAGE of partial purified of Rand protease by Octyl-Sepharose chromatography. Lane M: Molecular mass marker proteins Lane 1: Crude enzyme of *B. subtilis* isolate Rand Lane 2 and 3: Elution step in HIC.

The purification of the protease from the isolate Rand was increased to 1.8 fold with 72.7% recovery (Table 3). To check the homogeneity of the protein, the eluted peaks were separately pooled and subjected on the SDS-PAGE. The peak showed 5 bands on the SDS-PAGE with different molecular weight sizes as illustrated in FIG. 23.

Gel Filtration Chromatography

Gel filtration is used in fractionation mode to separate multiple components in a sample on the basis that the differences in their sizes can be used directly after any of the chromatography techniques. High resolution fractionation by gel filtration is well-suited for the final polishing step in a purification scheme and monomers can be separated from aggregates.

Figure 24:
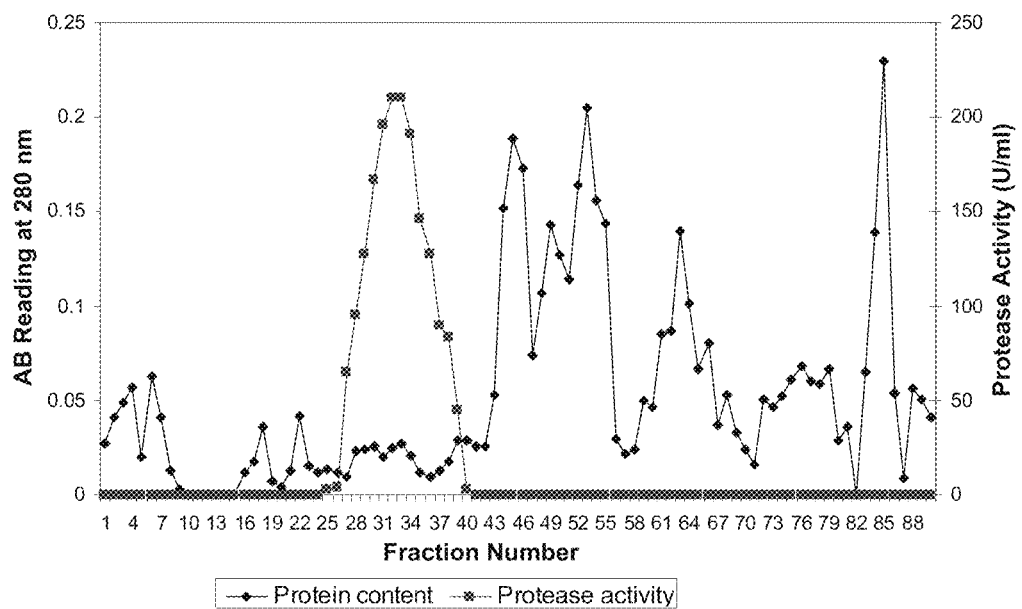
FIG. 24 shows purification profile of Rand protease on Sephadex G-75 chromatography.
Figure 25:
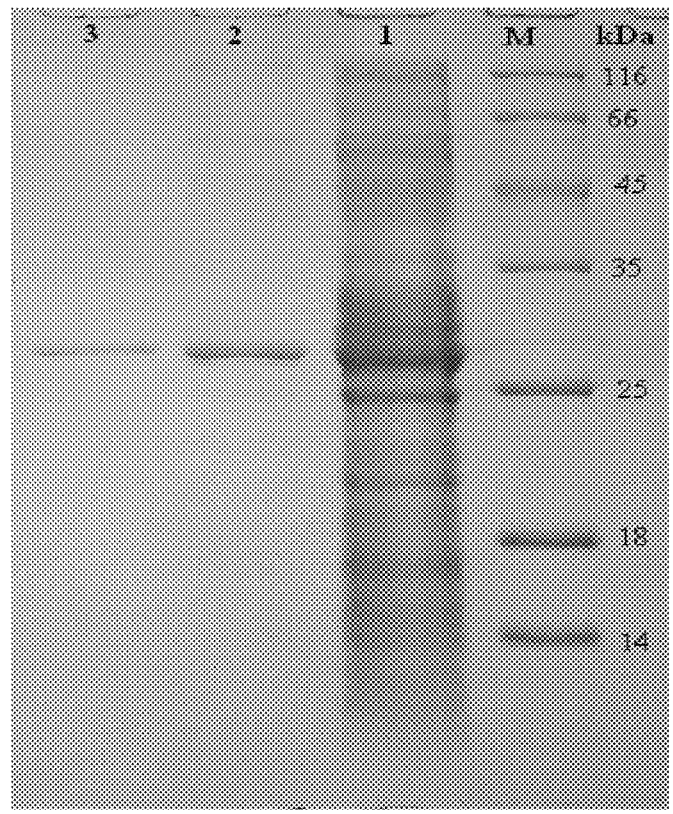
FIG. 25 shows SDS-PAGE purified of Rand protease by Sephadex G-75 chromatography.

Large molecules do not enter the gel pores and travel with mobile phase very quickly while smaller molecules can enter the pores (depending on their sizes) which then move much slowly. This final step of purification on the gel filtration chromatography column was found to produce the elution profile as shown in FIG. 24. The results of the protease purification are summarized in Table 3. A total of 60.5% of the activity units could be recovered and approximately 19.3 fold purification of the protease was achieved. The purity of the Rand protease was confirmed by the SDS-PAGE which demonstrated a single band, as illustrated in FIG. 25.

An enzyme solution from HIC column was loaded on a Sephadex G-75 gel filtration column (diameter 1.6: height, 64 cm) (Amersham Pharmacia Biotech, Uppsala, Sweden) pre-equilibrated with 2 column volume of Phosphate buffer (50 mM, pH 7.0). The chromatography procedure was conducted according to manufacture's instruction (Amersham Pharmacia Biotech, Uppsala, Sweden). The elution was carried out in the same buffer at a flow rate of 0.5 ml/min. Fraction (approximately 1.5 ml of each) that exhibited protease activities were collected. The active protease fractions were analyzed for protease activity, protein concentration, and SDS PAGE electrophoresis.

Proteases from other strains of Bacillus species were also purified. Serine protease from Bacillus mojavensis was purified 17 fold as unbound fractions using a single step anion exchange chromatography on the Q-Sepharose column. The recovered activity of the thiol-dependent serine alkaline protease is 37.2% (Beg and Gupta, 2003). A thermophilic neutral protease from thermophilic Bacillus strain HS08 was purified 4.25 fold and had a yield of 5.1% by ammonium sulphate precipitation, with columns of DEAE-Sepharose anion exchange chromatography and Sephacryl S-100 (Guangrong et al., 2006). Alkaline proteases, AP-1 and AP-2 from alkalophilic Bacillus sp. were purified 21.0 and 27.7 folds, respectively by a combination of ion exchange, ammonium sulphate precipitation and gel filtration. The recoveries of the purified alkaline serine proteases were 7.5% and 6.0% (Kumar et al., 1999). Serine alkaline protease from Bacillus pumilus CBS was purified 38 folds with 12% recovery, using the salt precipitation and gel filtration in a high-performance liquid chromatography (Jaouadi et al., 2008).

Determination of Protein Content

The protein content was determined by the Bradford (1976) using bovine serum albumin (BSA: Sigma Chemical Co., St. Louis, Mo., USA) as the standard. During the column

TABLE 3

Purification Table of the Protease

| Purification Steps | Volume (ml) | Activity (U/ml) | Total Activity (U) | Protein (mg/ml) | Total Protein (mg) | Specific Activity (U/mg) | Recovery (%) | Purification (Fold) |
|---|---|---|---|---|---|---|---|---|
| Crude | 40 | 215 | 8600 | 0.28 | 11.2 | 757.9 | 100 | 1.0 |
| Sepharose | 22 | 284 | 6248 | 0.2 | 4.4 | 1420 | 72.7 | 1.8 |
| Sephadex G-75 | 32.5 | 160 | 5200 | 0.1 | 0.35 | 14857.14 | 60.5 | 19.3 | chromatography, the concentrations on protein in the fractions were monitored by measuring their absorbance at 280 nm wavelength.

The Characterization of Purified Rand Protease

The Molecular Weight Determination

After each purification step, the purity of the protease fractions and their molecular masses were analyzed with a 6 to 12% sodium dodecyl sulphate-polyacrylamide gel electrophoresis (SDS-PAGE) according to the method of Laemmli (1970). The purified enzyme was prepared by acid precipitation with an equal volume of TCA (10%). The protein was pelleted by centrifugation at 14,000 rpm and 4° C. for 10 min, and the supernatant discarded. The pellet was then washed with cold phosphate buffer (pH 7.0) and recentrifuged at the same speed. Preparation of precipitated sample in reducing SDS sample buffer (1.25 ml of Tris-Cl (0.5 M, pH 6.8), 2.5 ml of glycerol 100% (v/v), 2.0 ml of SDS 10% (w/v), 0.2 ml of bromophenol blue 0.5% (w/v) and 3.55 ml $dH_2O$) was carried out by adding 50 µl β-Mercaptoethanol to 950 µl sample buffer prior to used. 30 µl sample buffer was added to the precipitated sample and followed by heating at 95° C. for 10 min. Each well of gel was loaded with 15 µl of protein in sample buffer and run in running buffer (g/L of Tris; 3.0, glycine; 14.4, and SDS; 1.0) under a constant voltage at 210 volt (30 mA) for approximately 1 hour and 15 min. The gel was stained with coomassie brilliant blue and destained.

Figure 26:
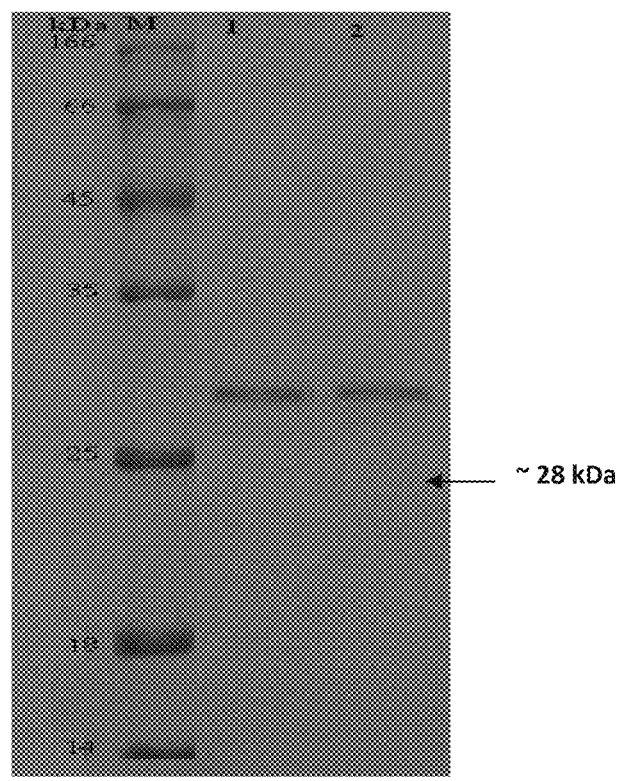
FIG. 26 shows molecular weight determination of Rand protease by SDS-PAGE.

The molecular mass of the Rand protease was estimated on the SDS-PAGE. The SDS-PAGE, Rand protease showed a single band corresponding to the molecular mass of approximately 28 kDa (FIG. 26). The molecular weight of Rand protease is different from most of the other *Bacillus* proteases, such as the serine protease from *B. subtilis* PE-11 (15 kDa) (Adinarayana et al., 2003), organic solvent stable protease from *Bacillus licheniformis* RSP-09-37 (55 kDa) (Sareen and Mishra, 2008), the metalloproteases from *B. cereus* KCTC3674 (36 and 38 kDa) (Kim et al., 2001), a solvent stable metalloprotease from *Bacillus* sp. TKU004 (27 and 57 kDa) (Wang et al., 2006a) and serine alkaline protease from *B. pumilus* CBS (34 kDa) (Jaouadi et al., 2008).

The Effect of Temperature on the Protease Activity and Stability

For investigation of the optimum temperature, the protease activity was measured using a standard protease assay procedure at different temperatures (37, 40, 45, 50, 55 60, 65 and 70° C.). The temperature stability of Rand protease was tested by assaying the remaining activity after 10, 20 and 30 min incubation at various temperatures 45, 50, 55, 60 and 65° C. in Tris-Cl (50 mM, pH 7.0) buffer. Samples were removed after incubation and chilled in ice bath. The remaining activity was measured by a slight modification method of Rahman et al. (1994).

Figure 27:
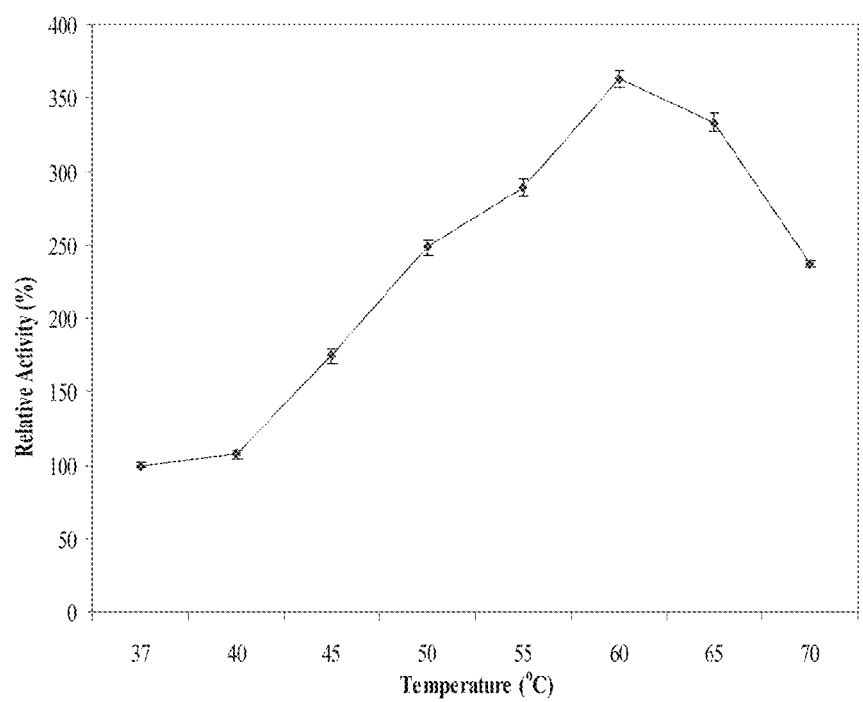
FIG. 27 shows effect of temperature on protease activity. Rand protease was assay at different temperatures. The activity at 37° C. was taken as 100%.

Using azocasein as a substrate, the optimum proteolytic activity of the Rand protease was determined to be at 60° C. (FIG. 27). Rand Protease underwent a thermal activation above 40° C. with the maximum activity found between 60 and 65° C. A similar optimum temperature between 60 and 65° C. for other *Bacillus* proteases has been observed by many other researchers. The protease from *B. subtilis* RM615 showed the optimum temperature and was found to be the most active at 60° C. (Moon et al., 1994). Meanwhile, the neutral protease from the thermophilic *Bacillus* strain HS08 which showed the optimum temperature at 65° C. (Guangrong et al., 2006). Serine alkaline protease from *Bacillus mojavensis* showed the optimum temperature at 60° C., with a rapid loss of activity above 65° C. (Beg and Gupta, 2003).

Meanwhile, the organic solvent-stable alkaline protease from *Bacillus licheniformis* showed the optimum temperature at 60° C. (Li et al., 2009).

Based on the comparison with the literature review on the characteristics of *Bacillus* strains producing proteases, it is determined that most of the *Bacillus* strains have different optimum temperatures. For instance, Gouda (2006) reported that the protease from *Bacillus* sp. MIG was thermostable as indicated by the optimum temperature of the pure enzyme at 50 and 55° C. The higher temperature optima up to 75° C. have been reported for alkaline protease from *B. stearothermophilus* F1 (Rahman et al., 1994). Organic solvent stable protease from *P. aruginosa* PST-01 exhibited the optimum temperature at 55° C. (Ogino et al., 1999). Sareen and Mishra (2008) also reported that the optimum temperature of the organic solvent stable protease from *Bacillus licheniformis* RSP-09-37 was 50° C. An organic solvent stable protease from *P. aeruginosa* PseA showed the optimum temperature and was found to be the most active at 60° C. (Gupta et al., 2005).

Figure 28:
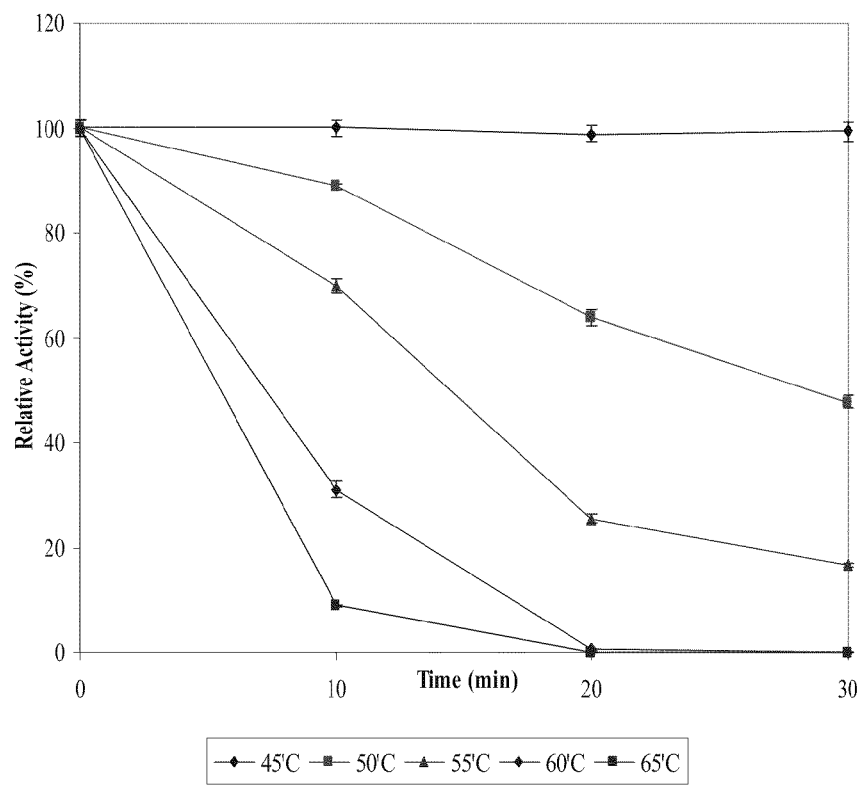
FIG. 28 shows thermal stability of Rand protease at various temperatures. Purified Rand protease was incubated at different temperatures for 30 min and remaining activity was measured at 60° C. The activity at 37° C. has been taken as 100%.

The thermal stability of Rand protease was tested by assaying the remaining activity after incubation at various temperatures ranging from 45 to 65° C. for 10, 20 and 30 min of incubation (FIG. 28). Rand Protease was found to be stable at 45° C. for 30 min and about 64% of the activity remained after 20 min of incubation at 50° C. In other reports, it was shown that Rand protease was more stable than the stability of the solvent protease from *P. aeruginosa* PseA which lost about 33% and 80% activities in 10 min of incubation at 65° C. and 70° C. (Gupta et al., 2005). Ghorbel et al. (2003) found that the protease from *Bacillus cereus* BG1 retained 89.5% of its original activity after 15-min incubation at 55° C. in the presence of 2 mM $Ca^{2+}$, while no activity was detected in the absence of $Ca^{2+}$. However, the thermal stability of Rand protease is lower compared to serine alkaline protease from *Bacillus mojavensis* exhibited half-life of 150 min, 15 min and 7 min at 60° C., 65° C. and 70° C., respectively (Beg and Gupta, 2003). The protease from thermophilic *Bacillus* strain HS08 was found stable during the 1 h incubation at 50° C. (Guangrong et al., 2006). Therefore, it could be hypothesized that a higher optimum temperature does not necessary mean a higher thermostability.

The Effect of Organic Solvents on the Protease Activity

The effects of organic solvents with various log P on protease activity were determined. The organic solvents used were n-dodecane (log P 6.6), diethyleether (log P 4.3), p-xylene (log P 3.1), toluene (log P 2.5), chloroform (log P 2.0), benzene (log P 2.0), acetone (log P 0.23), butanol (log P 0.8) and ethanol (log P 0.24). The control was done in the absent of organic solvent and assay under the same experimental conditions. The protease was incubated in the presence of 25% (v/v) of organic solvents for 30 min. The incubation was performed at 37° C. in water bath shaker with 150 rpm. The samples were removed and immediately vortex prior to assay the protease activity. Protease activity was determined by a slight modification method of Rahman et al. (1994).

Figure 29:
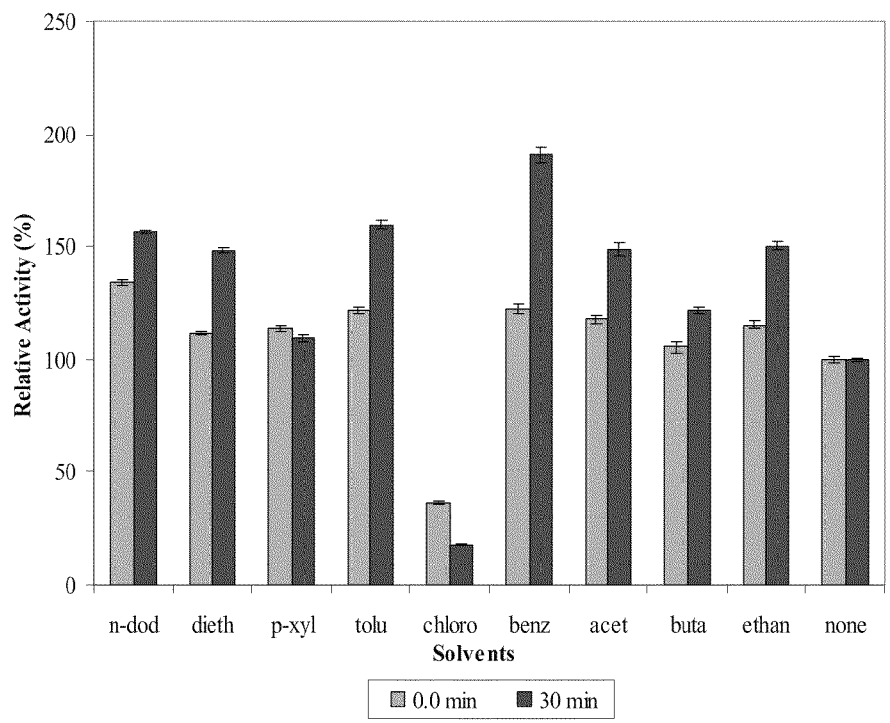
FIG. 29 shows effect of various organic solvent on protease activity. log P value of organic solvents. n-dodecane (6.6), Diethyleether (4.3), p-xylene (3.1), Toluene (2.5), Chloroform (2.0), Benzene (2.0), Acetone (0.23), Butanol (0.8) and Ethanol (0.24). Three ml of purified Rand protease were incubated with 1 ml of different organic solvents at 37° C. with shaking at 150 rpm for 30 min. The activity of the enzyme without any solvent (none) was taken as 100%.

A relative activity remaining after 30 min of incubation in 25% (v/v) of organic solvent is as shown in FIG. 29. In the present of diethyleether (Log P 4.3), p-xylene (Log P 3.1), acetone (Log P 0.23) and butanol (Log P 0.8) Rand protease retained more than 100% of its activity. The Rand protease activity increased in the presence of benzene (Log P 2.0) to 190%. In the present of chloroform (Log P 2.0), the protease activity was reduced to 18%. Meanwhile, the protease activity, in the present of n-dodecane (Log P 6.6), toluene (Log P 2.5) and ethanol (Log P 0.24), retained more than 150% of its activity. This level of stability towards hydrophobic and hydrophilic solvents is unique.

Rand Protease was found to be stable in the presence of organic solvents; however, the relationship between the stability against organic solvent and solvent polarity (log P value) of the added organic solvent was not found. This might be due to the fact that the stability of the protease in chloroform and benzene (both having log P=2.0) which are significantly different. Other similar results also reported that the stability protease was quite different in chloroform and benzene (Ogino et al., 1995; Tang et al., 2008). PseA protease was found to be stable in the presence of various organic solvent; however, the relationship between stability against organic solvent and solvent polarity (log P value) of the added organic solvent was not found (Gupta et al., 2005). Gubta and Khare reported that crude P. aeruginosa PseA protease showed a remarkable stability in the presence of most solvents having logarithm of the partition co-efficient (log P) above 2.0, but less stable in the presence of hydrophilic solvents (Gubta and Khare, 2007). Karadzic et al. (2004) reported that just over 20% of a metalloprotease activity from Pseudomonas aeruginosa remained in the presence of butanol, chloroform and hexane. Ogino et al. (1995) discovered that the stability of the Pseudomonas aeruginosa protease in the presence of organic solvents, of which the values of the log P were ≥3.2, was almost the same as when it was in the absence of organic solvents. The protease from Pseudomonas aeruginosa stain K was shown to be activated as compared to the control in the presence of 25% organic solvents with the Log P values over 4.0 (Rahman et al., 2005a). Indeed, protease from isolate Rand was not only stable in the presence of various organic solvents with the Log P values ≥2.0, but also in the presence of organic solvents with the Log P values below 2.0. These results indicated that this protease might be a novel solvent-stable protease.

The Effect of pH on the Protease Activity and Stability

Figure 30:
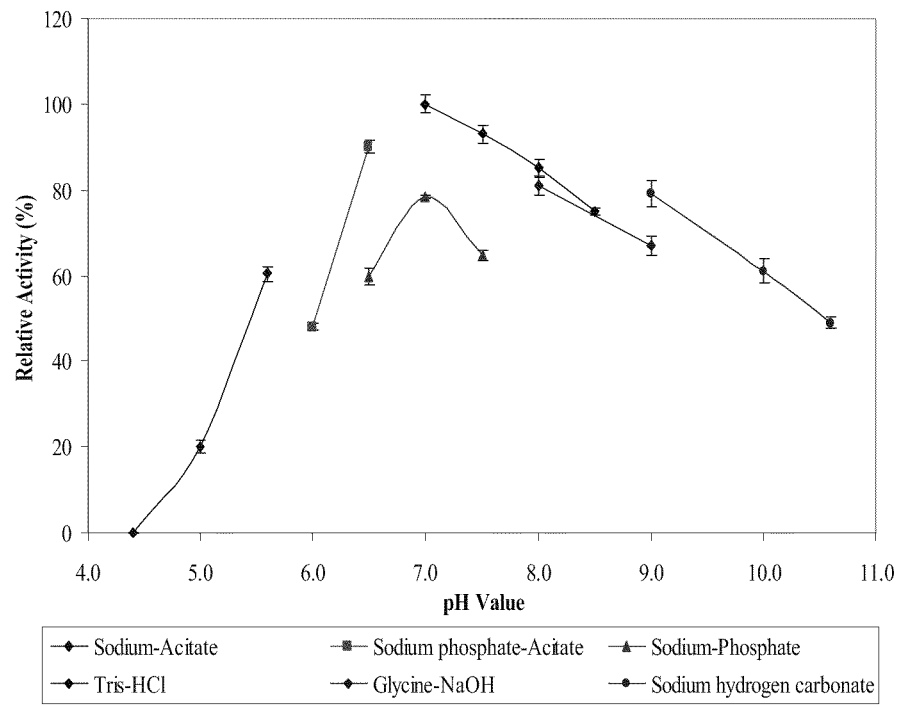
FIG. 30 shows effects of pH on protease activity. Sodium acetate buffer from pH 4.4 to 5.6; sodium phosphate acetate buffer pH 6.0 and 6.5; sodium phosphate buffer from pH 6.5 to 7.5; Tris-Cl buffer from pH 7.0 to 8.5); glycine-NaOH buffer from pH 8.0 to 9.0 and sodium hydrogen carbonate buffer from pH 9.0 to 10.6. Purified Rand protease was assayed at different pH values. The highest activity was taken as 100%.

Optimum pH of protease activity was determined by assaying Rand protease at different pH values. Buffer systems used were 50 mM sodium acetate (pH 4.4-5.6), 50 mM sodium phosphate acetate (pH 6.0 and 6.5), 50 mM sodium phosphate (pH 6.5-7.5), 50 mM Tris-Cl (pH 7.0-8.5), 50 mM glycine-NaOH (pH 8.0-9.0), and 50 mM sodium hydrogen carbonate (pH 9.0-10.6). Azocasein as a substrate was dissolved in different pH of buffers ranging from pH 4.4 to 10.6 Protease activity was determined by a slight modification method of Rahman et al. (1994). The pH stability of Rand protease was studied by assaying the remaining activity after incubation at various pHs ranging from pH 5.0 to 10.6 at 25° C. for 30 min. The remaining activity was measured by a slight modification method of Rahman et al. (1994). Rand protease showed its optimum protease activity toward azocasein at pH 7.0 in 50 mM Tris-Cl buffers (FIG. 30). Based on this observation, Rand protease could be classified as a neutral protease. Rand protease exhibited more than 50% of the relative activity between pH 5.6 to 10.0 and the protease activity was found to rapidly decrease when the pH values became less than pH 5.6 and more than pH 10. A solvent stable metalloprotease from Bacillus sp. TKU004 was found to have a similar pH optimum with Rand protease, which is pH 7.0. The protease was found to be active in the range of pH 6.0 to 8.0 (Wang et al., 2006). Guangrong et al. (2006) reported that the protease from thermophilic Bacillus strain HS08 exhibited the optimum pH at 7.5 in glycine-NaOH buffer (Guangrong et al., 2006).

In other reports, the proteases from Bacillus mujanvesis and Bacillus sp. showed the optimum pH at 10.5, 11.0 for AP-1 and 12.0 for AP-2 (Beg and Gupta, 2003; Kumar et al., 1999). Meanwhile, the protease from P. aeruginosa san-ai showed the optimum pH at 9.0 in 50 mM Tris-Cl buffer towards casein and is an alkaline protease (Karadzic et al., 2004).

Figure 31:
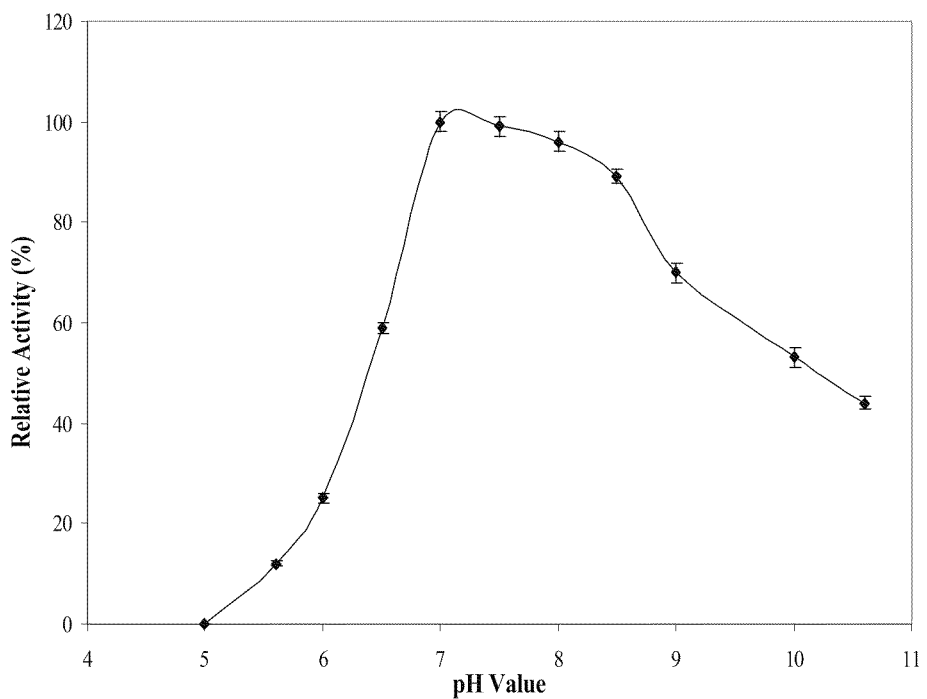
FIG. 31 shows effects of pH on protease stability. Sodium acetate buffer from pH 4.4 to 5.6; sodium phosphate acetate buffer pH 6.0 and 6.5; sodium phosphate buffer from pH 6.5 to 7.5; Tris-Cl buffer from pH 7.0 to 8.5); glycine-NaOH buffer from pH 8.0 to 9.0 and sodium hydrogen carbonate buffer from pH 9.0 to 10.6. Purified Rand protease was incubated at different pH values for 30 min. Remaining activity was measured at 37° C. The highest activity was taken as 100%.

Rand protease was found to be stable in broad range, from pH 6.5 to 10.0 with more than 50% relative activity after 30 min incubation (FIG. 31). Rand protease has similar pH stability with other protease from Bacillus reported by many researchers. Ghorbel et al. (2003) reported that protease from Bacillus cereus BG1 was stable in pH 6.0 to 9.0. The protease from Bacillus subtilis ITBCCB148 was stable in the pH range of 6.0 to 9.0 (Yandri et al., 2008). Metalloprotease from Pseudomonas sp. P96-47 strain which belongs to the neutral protease, as the protease exhibits the maximal pH stability and activity between pH 6.0 to 10.0 (Vazquez et al., 2008). In contrast, the protease from Bacillus mojanvesis was stable between pH 7.5 and 11.5 for more than 48 h (Beg and Gupta, 2003). Meanwhile after incubation for 240 min, proteases from Bacillus sp were stable over broad pH range of pH 6.0 to 12.0 (Kumar et al., 1999).

The Effect of Inhibitors on the Protease Activity

Figure 32:
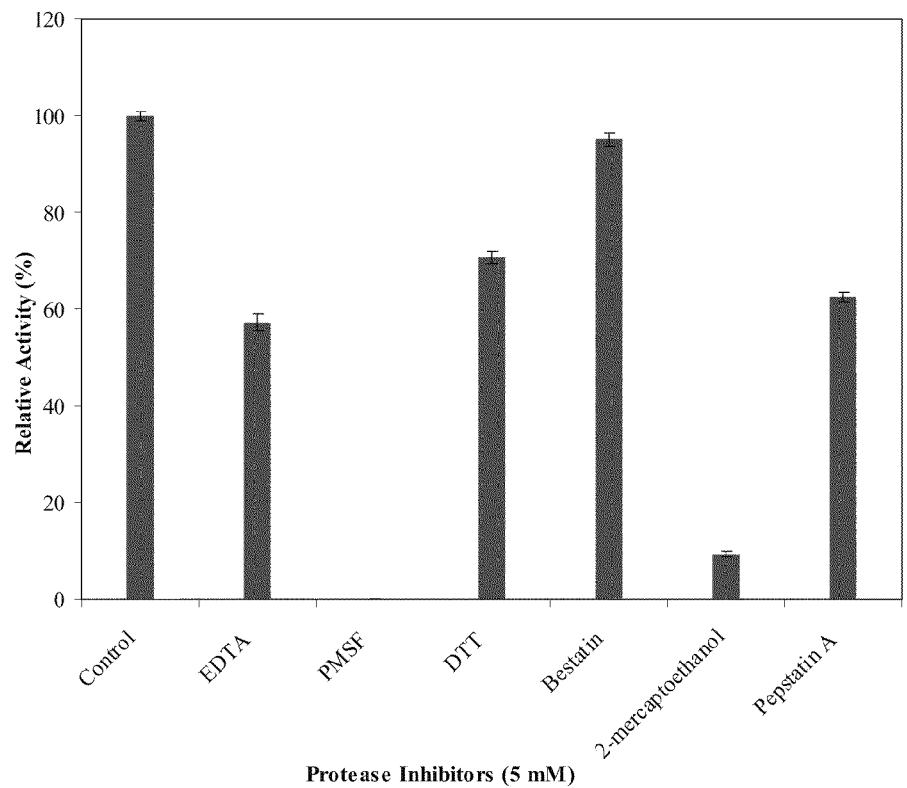
FIG. 32 shows effect of inhibitors on protease activity. Purified Rand protease was incubated with 5 mM of different inhibitors at 37° C. for 30 min.

The effect of various inhibitor ethylenediaminetetraacetic acid (EDTA), bestatin, pepstatin A, phenylmethanesulfonyl fluoride (PMSF), 1,4-Dithio-$_{DL}$-threitol (DTT), and 2-Mercaptoethanol were determined by incubating them with Rand protease for 30 min at 37° C. All the inhibitors were used at 5 mM final concentration. Protease activity was determined by a slight modification method of Rahman et al. (1994). The effect of different inhibitors on the protease activity of the Rand protease is as shown in FIG. 32. The activities, after incubation with different inhibitors, have been expressed to be relative to the control. Rand protease was completely inhibited by PMSF. This indicated to the presence of active serine residue in the catalytic site of the enzyme, therefore showing that the Rand protease belongs to the serine proteases family. About 90% reduction of the protease activity was shown in the present of 2-mercaptoethanol inhibitor; meanwhile, Rand protease exhibited 30% reduction of protease activity in the present of DTT inhibitor. On the contrary, the metal chelator agent inactivated the protease activity to about 43% inhibition. The protease activity was retained to about 95% and 63% in the present of aminopeptidases (Bestatin) and aspartic proteases inhibitor (Pepstatin A).

Similar results of serine proteases, which were completely inhibited by PMSF, were observed in serine alkaline protease produced by Bacillus pumilus CBS (Jaouadi et al., 2008), Serine alkaline protease from Bacillus subtilis PE-11 (Adinarayana et al., 2003), serine protease produced by Geobacillus sp. YMTC 1049 (Zhu et al., 2007) and an organic solvent-tolerant serine protease by Bacillus sp. RKY3 (Reddy et al., 2008). It is important to highlight that PMSF is the only inhibiting protease activity of Bacillus sp. (Kumar et al., 1999). Reducing agents, such as DTT and 2-mercaptoethanol, have been used to split the disulfide bonds of proteins. The inhibition of Rand protease activity by DTT and 2-mercaptoethanol suggested that the Rand protease contains disulfide bond in the protein structure. Meanwhile, the EDTA has been shown to be a general inhibitor for the neutral proteases as it is inhibitory on Rand protease. P. aeruginosa san-ai protease was strongly inhibited by both EDTA and DTT. The inhibition suggests that the protease is a metalloprotease and contains disulfide bond in the protein structure (Karadzic et al., 2004). The protease from P. aeruginosa PST-01 was inhibited by EDTA and 1,10-phenantroline. Thiol protease inhibitor such as PCMB partially inhibited PST-01 protease activity (Ogino et al., 1999).

Effect of Metal Ions on Protease Activity

Figure 33:
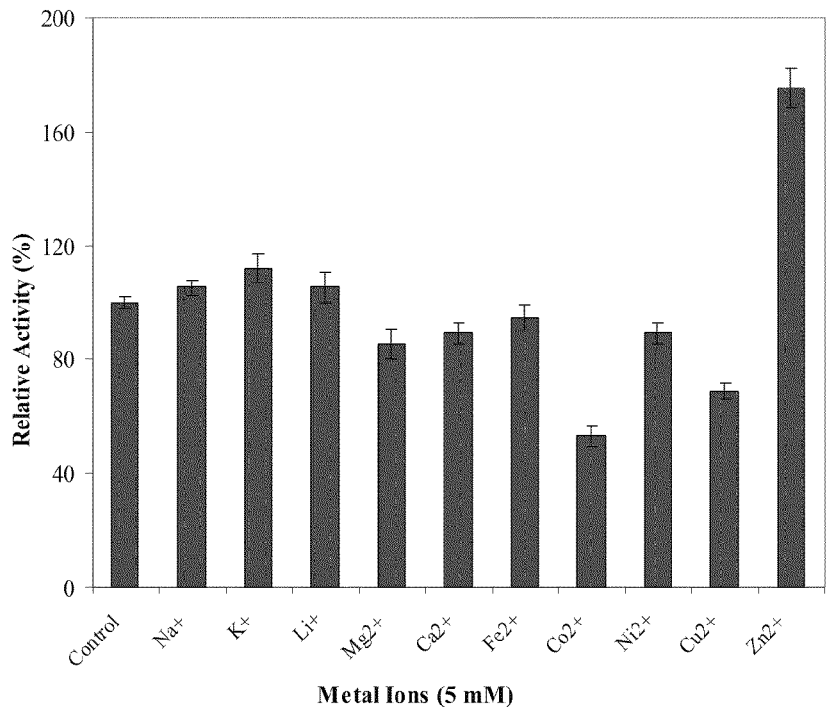
FIG. 33 shows effect of metal ion on protease activity. Purified Rand protease was treated with 5 mM of various metal ions at 37° C. for 3 min.

The effect of metal ions on protease activity was determined by incubating the protease with different metal ions at 5 mM final concentration. The metal ions used were $K^+$, $Na^+$, $Mg^{2+}$, $Ca^{2+}$, $Mg^{2+}$, $Fe^{2+}$, $Co^{2+}$, $Cu^{2+}$, $Zn^{2+}$ and $Li^+$. The samples were incubated at 37° C. for 30 min. Protease activity was determined by a slight modification method of Rahman et al. (1994). The control contained no ions. The effects of various metal ions on the Rand protease activity are presented in FIG. 33. Among these metal ions, $Zn^{2+}$ was found to stimulate protease activity by around 175%. The protease activity was slightly enhanced by around 105%, 112% and 105% respectively for $Na^+$, $K^+$ and $Li^+$. The inhibitory effects of $Mg^{2+}$, $Fe^{2+}$ and $Ni^{2+}$ were less as compared to that of $Co^{2+}$ and $Cu^{2+}$. The present $Ca^{2+}$ showed the inhibitory effect on the enzyme, decreasing the activity to around 89% of the control. This finding explained that Rand protease did not require the presence of $Ca^{2+}$ ions to be active. This observation is similar with that of Guangrong et al. (2006) who reported that $Ca^{2+}$ ions did not show any influence on the proteolytic activity of serine protease from thermophilic Bacillus strain HS08. Similar reports on the effects of metal ion for other Bacillus proteases have also been observed by view researchers. In another study by Wang et al. (2006a), only zinc ions were reported to efficiently restore the activity of the apo-enzyme to 75% of the original level, suggesting that zinc is essential for Bacillus sp. TKU004 protease. Meanwhile, the protease activity of thermophilic Bacillus strain HS08 protease was enhanced by 2 mM $Zn^{2+}$, where the relative activity was recorded to be 109% (Guangrong et al., 2006). In contrast, a strong inhibitory effect on the protease activity of B. megaterium was observed in the presence of $Zn^{2+}$, with relative activities of 28% (Yossan et al., 2006). Furthermore, zinc which usually serves as a co-factor of many enzymes, could be replaced by heavy metals, thereby making the enzymes inactive (Donaldson, 1991). However, a high concentration of $Zn^{2+}$ in mM range often inhibits metalloproteinases. The inhibition by $Zn^{2+}$ is due to the formation of zinc monohydroxide that bridges the catalytic zinc ion to a side chain in the active site of the enzyme (Salvesen and Nagase, 1989). It is, therefore, reasonable to conclude that the protease of this study is a $Zn^{2+}$-activated serine protease.

Substrate Specificity of Rand Protease

Figure 34:
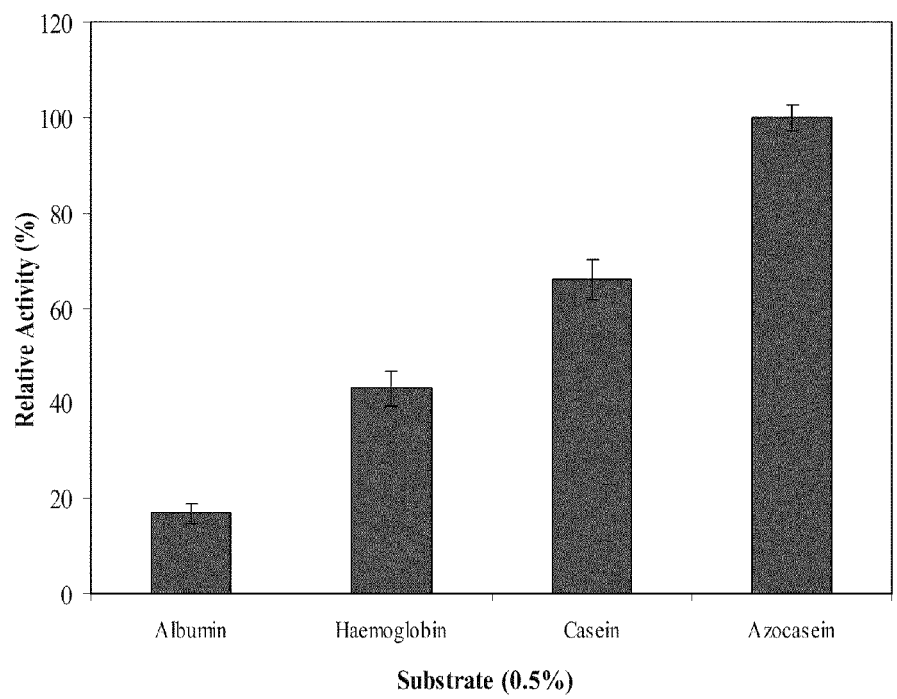
FIG. 34 shows substrate specificity of protease Rand. Purified Rand protease was incubated with different substrates at 37° C. for 30 min. Activity against azocasein was taken as 100%.

The substrate specificity of the Rand protease toward natural substrate (casein, albumin, haemoglobin and azocasein) was determined at 0.5% (w/v). 200 µl of enzyme was added into 1 ml of substrate vial bottle. Blank reagent as a control for each substrate was done by replacing the enzyme solution with buffer Tris-Cl (0.1 M), CaCl (2 mM) pH 7.0. The reaction mixtures were incubated at 37° C. for 30 min in water bath shaker under shaking at 150 rpm. The reaction was terminated by adding 1.2 ml of Trichloroacetic Acid (TCA) 10% (w/v) and allowed to stand at room temperature (25-27° C.) for 30 min. The precipitate protein was centrifuged at 13000×g for 10 min. Protease activity was determined by a slight modification method of Rahman et al. (1994). Absorbance of supernatant for casein, albumin and haemoglobin were measured at wavelength 280 nm. The natural substrate specificity of the purified Rand protease is shown in FIG. 34. This Rand protease was capable of hydrolyzing all the soluble and insoluble substrates such as albumin, haemoglobin, casein and azocasein to a significant extent with the maximum specificity toward azocasein. It is evident that the protease has a better digestive ability on azocasein than that on casein, haemoglobin or albumin. A similar observation had been reported by Guangrong et al. (2006) who found out that serine protease from thermophilic Bacillus strain HS08 showed substrate specificity to azocasein.

The invention claimed is:

1. A purified protease obtained from *Bacillus subtilis* isolate Rand, a representative sample of which has been deposited as CCTCC accession number M2013058, having the following properties:
   a) an apparent molecular weight of 28 kD determined by SDS-PAGE;
   b) a pH stability with buffers ranging from pH 5 to pH 11 at 25° C.;
   c) a working temperature in the range between 37° C. and 70° C. at pH 7.0;
   d) organic solvents stability of 25% (v/v) of organic solvents ranging from a log P of 0.8 to a log P of 8.8 for 30 min and at 37° C.;
   e) working inhibitors including ethylenediaminetetraacetic acid (EDTA), bestatin, pepstatin A, phenylmethanesulfonyl fluoride (PMSF), 1,4-Dithio-$_{DL}$-threitol (DTT), and 2-Mercaptoethanol for 30 min at 37° C.;
   f) working metal ions such as $K^+$, $Na^+$, $Mg^{2+}$, $Ca^{2+}$, $Mg^{2+}$, $Fe^{2+}$, $Co^{2+}$, $Cu^{2+}$, $Zn^{2+}$ and $Li^{2+}$ and
   g) substrate specificity with natural substrate including casein, albumin, haemoglobin and azocasein, the stability of the purified protease is substantially 100%; with azocasein after 30 minutes incubation at 37° C.

2. The purified protease of claim 1, wherein the buffers including sodium acetate, sodium phosphate acetate, sodium phosphate, Tris-Cl, glycine-NaOH and sodium hydrogen carbonate.

3. The purified protease of claim 1, wherein the temperature having an optimum value of 60° C.

4. The purified protease of claim 1, wherein the organic solvents includes n-dodecane (log P 6.6), diethyleether (log P 4.3), p-xylene (log P 3.1), toluene (log P 2.5), chloroform (log P 2.0), benzene (log P 2.0), acetone (log P 0.23), butanol (log P 0.8) and ethanol (log P 0.24).

5. The purified protease of claim 1, wherein the purified protease is thermostable and organic solvent tolerant.

* * * * *